(12) United States Patent
Zang et al.

(10) Patent No.: US 8,153,065 B2
(45) Date of Patent: Apr. 10, 2012

(54) FLOURESCENT ORGANIC NANOFIBRILS BASED ON ARYLENE-ETHYLENE MACROCYCLES AS SENSORY MATERIALS FOR EXPLOSIVES DETECTION

(75) Inventors: Ling Zang, Carbondale, IL (US);
Jeffrey Moore, Urbana, IL (US);
Tammene Naddo, Carbondale, IL (US);
Wei Zhang, Cambridge, MA (US)

(73) Assignee: Southern Illinois University, Carbondale, IL (US)

( * ) Notice: Subject to any disclaimer, the term of this patent is extended or adjusted under 35 U.S.C. 154(b) by 664 days.

(21) Appl. No.: 12/110,869

(22) Filed: Apr. 28, 2008

(65) Prior Publication Data

US 2009/0233374 A1 Sep. 17, 2009

Related U.S. Application Data

(60) Provisional application No. 60/926,555, filed on Apr. 27, 2007.

(51) Int. Cl.
*G01N 21/64* (2006.01)
(52) U.S. Cl. .............. 422/82.08; 422/82.05; 422/400; 422/425; 436/164; 436/166
(58) Field of Classification Search ........... 436/164–166
See application file for complete search history.

(56) References Cited

OTHER PUBLICATIONS

Balakrishnan et al. "Nanofibril Self-Assembly of an Arylene Ethynylene Macrocycle", J. Am. Chem. Soc. 2006, v. , pp. 6566-6567.*

* cited by examiner

*Primary Examiner* — Yelena G Gakh
(74) *Attorney, Agent, or Firm* — Polsinelli Shughart PC

(57) ABSTRACT

The present invention relates to a class of fluorescent, organic nanofibrils, and particularly the films comprising entangled piling of these nanofibrils exhibiting effective quenching of their fluorescence upon exposure the vapor of explosives. The invention also relates to a sensor and a method for sensing the explosives vapor and other volatile organic compounds, including the explosives taggants through the modulation of the fluorescence of the nanofibril film and the electrical conductivity of the nanofibrils. The invention also relates to a development of synthetic methods, protocols and techniques that leads to production of various arylene-ethynylene macrocycle (AEM) molecules, which consist of a shape-persistent, toroidal scaffold in planar conformation, with minimal ring strain and highly tunable ring sizes (from 0.5 nm to above 10 nm). The invention also relates to an approach to optimization of the one-dimensional molecular arrangement along the long axis of the nanofibril, which provides increased exciton (excited state) migration (via cofacial intermolecular electronic coupling) and charge transport (via pi-electronic delocalization). A combination of long-range exciton migration and efficient charge transport makes the nanofibrils ideal as sensory materials for detecting explosives and other volatile organic compounds through both optical and electrical sensing mechanisms.

15 Claims, 27 Drawing Sheets

FLOURESCENT ORGANIC NANOFIBRILS BASED ON ARYLENE-ETHYLENE MACROCYCLES AS SENSORY MATERIALS FOR EXPLOSIVES DETECTION

CROSS REFERENCE TO RELATED APPLICATIONS

This application claims priority from U.S. Provisional Application Ser. No. 60/926,555 filed on Apr. 27, 2007, which is hereby incorporated by reference in its entirety.

FIELD OF INVENTION

The present invention relates to a class of fluorescent, organic nanofibrils, and particularly the films comprising entangled piling of these nanofibrils exhibiting effective quenching of their fluorescence upon exposure to the vapor of explosives. The invention also relates to a sensor and a method for sensing the explosives vapor and other volatile organic compounds, including the explosives taggants through the modulation of the fluorescence of the nanofibril film and the electrical conductivity of the nanofibrils.

BACKGROUND OF THE INVENTION

Development of efficient sensing materials and techniques for detecting explosives has gained more attention now than ever due to the increasing worldwide terrorist threat. Among all the detection techniques available nowadays, fluorescence-quenching based chemical detection represents one of the most sensitive and convenient methods that have been widely employed in explosives identification.

Currently, aromatic molecules and conjugated polymers (when fabricated as films) are used in sensing explosives vapor via fluorescence quenching. However, the quenching efficiency of these materials is often limited by the short exciton diffusion due to the poor molecular organization and/or weak intermolecular electronic interactions. Creating sensor films that require different film thickness dependent on the desired results. Consequently, very thin films are needed to achieve desirable amplification of signal transduction, whereas a sufficiently thick film is usually required in order to produce a measurable fluorescence signature and to minimize the interference of photobleaching. Because of these limitations, there is a growing need to develop new sensing materials that enable long-range exciton migration, and thus produce sensing systems independent of film thickness and with more flexibility for device fabrication.

Meanwhile, there is a great need to develop new types of sensing materials or systems that provide increased sensitivity, as well as increased reliability (to minimize false positives) in explosives detection. The detection minimum that is set up by the Department of Homeland Security for an explosives detector or sensor is that it should be able to detect or identify the explosives source at a standoff position, which is 50 meters (ideally 100 meters) away from the explosives source. Additionally, detecting an underground landmine also demands improved efficiency in explosives sensing, as the vapor pressure of the explosives, particularly TNT, above an underground landmine is only around 40 ppt (part per trillion).

SUMMARY OF THE INVENTION

The present invention provides development of a new type of sensory materials that comprise fluorescent, organic nanofibrils, and particularly the films comprising entangled piling of these nanofibrils exhibiting effective quenching of their fluorescence upon exposure to the vapor of explosives. The nanofibrils are fabricated from various arylene-ethynylene macrocycles (AEMs), which consist of a shape-persistent, toroidal scaffold in planar conformation, with minimal ring strain and highly tunable ring sizes (from 0.5 nm to above 5 nm). The large-area planar molecular surface of AEMs enables effective long-range co-facial stacking between the molecules. Well-defined nanofibers with controllable diameter size (5-50 nm) and length (a few hundred nanometers to a few tens of microns) can be fabricated via expedient solution or surface based self-assembly. Through a combination of novel molecular design and engineering, and exquisite supramolecular assembly, the one-dimensional molecular arrangement can be controlled in a way leading to maximal electronic interaction between the molecules. Such one-dimensional molecular arrangement is highly favorable for exciton (excited state) migration (via intermolecular electronic coupling) and charge transport (via pi-electronic delocalization). The long-range exciton migration and charge transport intrinsic to the nanofiber enable development of multimode optoelectronic sensors that demand both amplified fluorescence quenching and large modulation of electrical current by surface adsorption of molecules that are of interest of detection.

When deposited on a suitable substrate, the AEM nanofibers form entangled piles, which in combination with the noncollapsible ring structure of AEM molecules, produce a film that possesses porosity on a number of length scales. A porous film consisting of a large number of nanofibers not only provides increased surface area for enhanced adsorption of gaseous molecules, but also enables expedient diffusion of guest molecules across the film matrix, leading to efficient sensing, with a signal potentially independent on the film thickness. Combination of these porous properties with the extended exciton migration intrinsic to the individual nanofibers makes the nanofibril film an efficient sensing material for detecting oxidative volatile organic compounds (VOCs), particularly explosives. Moreover, the newly available synthetic methods enable the preparation of AEM molecules that are highly tunable and adaptable with respect to structure, geometry, size and redox properties, providing enormous options for optimizing the crystalline structure, internal void dimensions and optoelectronic properties of the nanofibers to achieve the maximal sensitivity in optoelectronic sensing.

The present invention relates to organic nanofibrils capable of emitting radiation and exhibiting increased luminescent quantum yields, and the process for producing the nanofibrils. These nanofibrils can be fabricated with different diameter sizes (5-50 nm) and lengths (a few hundred nanometers to a few tens of microns), and can be fabricated via expedient solution or surface based self-assembly. Through a combination of novel molecular design and engineering, and exquisite supramolecular assembly, the one-dimensional molecular arrangement along the nanofibril can be controlled in a way leading to maximal electronic interaction between the molecules.

The invention also relates to a development of a sensory film that comprises entangled piles of the fluorescent organic nanofibrils. The entangled piling of the nanofibrils, in combination with the noncollapsible ring structure of the AEM molecule, produce a film that possesses porosity on a number of length scales. A porous film consisting of a large number of nanofibers not only provides increased surface area for enhanced adsorption of gaseous molecules, but also enables expedient diffusion of guest molecules across the film matrix, leading to efficient sensing, with a signal potentially independent of the film thickness.

The invention also relates to various novel arylene-ethynylene macrocycle (AEM) molecules and the process for the a development of synthesis methods, protocols and techniques that leads to production of various arylene-ethynylene macrocycle (AEM) molecules, which consist of a shape-persistent, toroidal scaffold in planar conformation, with minimal ring strain and highly tunable ring sizes (from 0.5 nm to above 10 nm). The newly developed synthesis enables the preparation of AEM molecules that are highly tunable and adaptable with respect to structure, geometry, size and redox properties, providing enormous options for optimizing the crystalline structure, internal void dimensions and optoelectronic properties (related to both optical and electrical properties) of the nanofibers to achieve the maximal sensitivity in optoelectronic sensing.

The invention also relates to a sensor and a method for sensing the explosives vapor and other volatile organic compounds, including the explosives taggants through the modulation of the fluorescence of the nanofibril film and the electrical conductivity of the nanofibrils.

The invention also relates to an approach to optimization of the one-dimensional molecular arrangement along the long axis of the nanofibril; organized one-dimensional molecular arrangement is highly favorable for exciton (excited state) migration (via intermolecular electronic coupling) and charge transport (via pi-electronic delocalization). The long-range exciton migration and charge transport intrinsic to the nanofiber enable development of multimode optoelectronic sensors that demand both amplified fluorescence quenching and large modulation of electrical current by surface adsorption of molecules that are of interest of detection.

The invention also relates to a combination of the porous properties of the nanofibril film with the extended exciton migration intrinsic to the individual nanofibers, making the nanofibril film an efficient sensing material for detecting oxidative volatile organic compounds (VOCs), particularly explosives.

DETAILED DESCRIPTION

Figure 1:
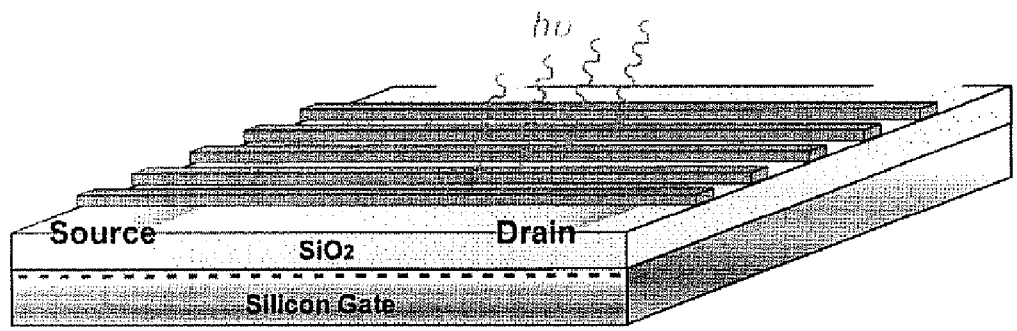
FIG. 1 shows a FET device fabricated with a pair of nanoelectrodes on a heavily doped silicon chip (serving as the back gate). The surface of the silicon is pre-covered with a layer of oxide with controllable thickness. Parallel aligned nanofibers will be deposited across the two electrodes by drop-casting.

The present invention relates to fluorescent organic nanofibril, the method of the nanofibrils and nanofibril films exhibiting enhanced optical properties such as luminescent efficiency, enhanced stabilities and devices such as sensors which incorporate these nanofibril films.

One aspect of the invention provides a sensor comprising a film. A "sensor" refers to any device or article capable of detecting an analyte. In one embodiment, the film comprises entangled piling of nanofibrils, where the nanofibrils comprise a large number of molecules assembled in crystalline phase. The nanofibril is capable of emitting radiation with a quantum yield that is sufficient to be detected by a regular fluorometer. The emission of the nanofibril is decreased upon exposure to explosives vapor and other oxidative molecules.

The molecules used in the creation of the nanofibrils and nanofibril films or sensors, are building-block molecules and are in the structure of arylene-ethynylene macrocycle (AEM), and have a backbone in planar, rigid, cyclic structure, where "backbone" refers to the longest continuous pi-conjugate-bond pathway of the molecule. The pi-conjugation provides strong adsorption and emission (i.e., fluorescence) of electromagnetic radiation (i.e., light irradiation). The pi-conjugation may be altered by the substitution of functional moieties at the backbones, thus leading to change in the wavelength and efficiency of the absorption and emission of the molecule. Typically, fluorescence is "quenched" when a chromophore in an excited state is exposed to an "acceptor" species that can absorb energy or draw an electron (or positive charge) from the excited state chromophore.

In one embodiment, the cyclic backbone of the AEM molecule can be in the shape of triangle, square, pentagon, or hexagon, and can be in different sizes, ranging from 0.5 nm to above 10 nm. The cyclic backbone can consist of different chemical groups at the corners, the chemical groups including different functional moieties, chromophores, and in different conjugate structure.

In one embodiment, the cyclic backbone of the AEM molecule can consist of different chemical groups at the edges, the chemical groups including different functional moieties, chromophores, and in different conjugate structure.

In one embodiment, the cyclic backbone of the AEM molecule can be modified by substitution with different chemical groups at the corners, the substitutions functioning as side chains, the side chains affecting the strength and conformation of the molecular arrangement within the nanofiber. The strength and conformation of the molecular arrangement affect the exciton (i.e., excited state) migration and charge transport along the nanofibril, and thus affect the sensing efficiency of the nanofibrils when used as fluorescent sensory materials.

In one embodiment, the cyclic backbone of the AEM molecule can be modified by substitution with different chemical groups at the edges, the substitutions functioning as side chains, the side chains affecting the strength and conformation of the molecular arrangement within the nanofiber.

In one embodiment, the cyclic backbone of the AEM molecule can be modified by substitution with different chemical groups at the corners, the substitutions can be connected to the backbone with different linkers, where the linkers may be in conjugation with the backbone, affecting the absorption and emission capability of the backbone, and the linker may also affect the configuration between the side chains and the backbone, resulting in different conformations of the whole molecule (including both the central backbone and all the side chains), the conformation affecting the strength and conformation of the molecular arrangement.

In one embodiment, the cyclic backbone of the AEM molecule can be modified by substitution with different chemical groups at the edges, the substitutions can be connected to the backbone with different linkers, where the linkers may be in conjugation with the backbone, affecting the absorption and emission capability of the backbone, and may also affect the configuration between the side chains and the backbone, resulting in different conformations of the whole molecule (including both the central backbone and all the side chains), the conformation affecting the strength and conformation of the molecular arrangement.

In one embodiment, the sensory film comprising nanofibrils is fluorescent, emitting light covering both ultraviolet and visible region. The film is also highly porous, providing strong adsorption and efficient diffusion for explosives molecules.

In one embodiment, the sensory film comprising nanofibrils can be fabricated by casting a solution containing the molecule onto a substrate, followed by drying in air and then vacuum at elevated temperatures. The concentration of the solution used for casting the film can be adjusted to afford different thickness of the film thus cast, and the density of the nanofibrils thus packed in the film. The substrate thus used can be a glass or any other substrate known in the industry such as a flat substrate that provides strong affinity with the molecules and nanofibrils.

In one embodiment, the sensory film comprising nanofibrils can be fabricated by drop-casting the nanofibrils suspended in a solvent onto a substrate, e.g., glass, followed by drying in air and then vacuum at elevated temperatures. The concentration of the nanofibrils in the suspension can be adjusted to afford different thickness of the film thus cast, and the density of the nanofibrils thus packed in the film. The nanofibrils can be prepared by a so-called 'phase transfer' method, which is based on slow crystallization, i.e., self-assembly of the building-block molecules, at the interface between a good and a poor solvent, where the good solvent is defined as a solvent that provides sufficient solubility for the molecules, and the poor solvent is defined as a solvent that provides no or limited solubility for the molecules. The 'phase transfer' can be performed by adding a large amount of the poor solvent atop a small volume of the solution in a good solvent, where the volume ratio of the poor and good solvent is at least 10:1 in volume, and the initial concentration of the solution in the good solvent can be adjusted to afford different sizes and lengths of the nanofibrils thus fabricated. The 'phase transfer' can also be performed by injecting a large amount of the poor solvent into a small volume of the solution in a good solvent, followed by mixing the two solvents mechanically, for which the volume ratio of the poor and good solvent is at least 10:1 in volume, and the initial concentration of the solution in the good solvent can be adjusted to afford different sizes and lengths of the nanofibrils thus fabricated.

In one embodiment, the nanofibrils can also be prepared by a sol-gel method, which is processed by dispersing the solid of the molecules in an appropriate solvent, followed by heating the solvent up to an elevated temperature till all the solid becomes dissolved, then cooling the solution slowly back to room temperature. Upon cooling to room temperature, the solution eventually becomes gelled, the gel thus formed becoming harder upon aging in air for extended time.

One aspect of the present invention provides a method for amplifying the fluorescence quenching, comprising: providing an article comprising nanofibrils having an energy migration pathway and absorption and emission capability; exposing the article to a light source to form an excited state (i.e., exciton); and allowing the exciton to travel through the migration pathway and to transfer to the quencher molecules adsorbed on the surface of the nanofibril, resulting in quenching of the exciton (i.e., quenching of the fluorescence of the nanofibril). The energy migration pathway includes the intermolecular pi-pi stacking that is primarily along the long axis of the nanofibril. The article comprises a thin film (in thickness of 10 to 200 nm) consisting of entangled piling of nanofibrils. The quencher molecule can be any analyte molecule of interest, particularly the explosives molecules, e.g., 2,4,6-trinitrotoluene (TNT) and 2,4-dinitrotoluene (DNT).

Another aspect of the present invention provides a method for amplifying the sensing of gaseous molecules, comprising: providing an article comprising nanofibrils having an energy migration pathway and absorption and emission capability; exposing the article to a light source to form an excited state (i.e., exciton); and allowing the exciton to travel through the migration pathway and to transfer to the gaseous molecules of interest that are adsorbed on the surface of the nanofibril, resulting in quenching of the exciton (i.e., quenching of the fluorescence of the nanofibril). The energy migration pathway includes the intermolecular pi-pi stacking that is primarily along the long axis of the nanofibril. The article comprises a thin film (in thickness of 10 to 200 nm) consisting of entangled piling of nanofibrils. The gaseous molecules are sensed (or detected) by measuring the change of the fluorescence of nanofibrils before and after exposure to the gaseous molecules.

Another aspect of the present invention provides a sensor film that demonstrates sensing efficiency independent on the film thickness, where the film consists of entangled piling of the nanofibrils, in thickness of 10 nm to 200 nm. The sensing efficiency is defined as the percentage of quenching of the fluorescence of the nanofibril film. The film-thickness-independence of the fluorescence quenching enables fabrication of a sensing film in a thickness that provides the best sensing efficiency and stability against photobleaching or photo oxidation.

In one embodiment, the sensory film demonstrates fast time response to exposure to explosives vapor, where the time response is defined as the time needed to reach the saturation of the fluorescence quenching of the film after exposure to the explosives vapor. For the films tested in the present invention the time response is about 10 seconds for exposure to TNT vapor at 5 ppb, or DNT vapor at 100 ppb. The quenching time response is faster than the other organic based sensory films, including those fabricated from polymers and other organic molecules.

In one embodiment, the sensory film demonstrates strong stability with regard to being repeatedly used in the explosives sensing via fluorescence quenching. The repeated use of the film in fluorescence quenching is performed by recovering the fluorescence of the film (after being used in fluorescence quenching) back to the level of the pristine film before being used in fluorescence quenching. The recovery of fluorescence of the film is processed by placing the film in open air for extended time or placing the film in a saturated vapor of hydrazine (140 ppm) for hours.

In one embodiment, the sensory film demonstrates strong stability against photobleaching or any other photo-damage.

The stability test is performed by exposing the film to light irradiation for different amount if times.

In one embodiment, the sensory film demonstrates efficient fluorescence quenching upon exposed to the vapor of explosives, including TNT and DNT, and the fluorescence quenching is primarily due to the electron transfer from the excited state of the nanofibril to the adsorbed gaseous molecules.

In one embodiment, the sensory film demonstrates efficient fluorescence quenching upon exposed to the vapor of explosives taggants, such as 2,3-dimethyl-2,3-dinitrobutane (DMNB), which are required additives in all legally manufactured explosives and plastic explosives devices. The fluorescence quenching is primarily due to the electron transfer from the excited state of the nanofibril to the adsorbed gaseous molecules.

In one embodiment, the sensory film demonstrates strong stability for operating under ambient conditions, the film being robust against air, moisture, and room light or sun light irradiation Another aspect of the present invention provides a sensor that is operated as a field-effect transistor (FET) in conjunction with light irradiation (FIG. 1), leading to a photo-modulated FET, thus termed as phototransistor in this invention. The nanofibrils are parallel aligned and connected between two electrodes, one termed as source and the other termed as drain, both source and drain electrode are fabricated on a doped silicon (serving as the back gate) that is covered with a thin layer of silicon oxide functioning as a insulating layer. The source and drain electrodes can be gold or other noble metals, and the two electrodes can be separated at variable distance ranging from nanometers to microns. The nanofibrils can be deposited atop or underneath the source and drain electrodes. The number of the nanofibrils used can be variable ranging from only one to a large number.

In one embodiment, the sensing mechanism is based on the modulation of the electrical conductivity, i.e., electrical current flowing through the nanofibrils, upon exposing the nanofibrils to gaseous molecules, such as explosives vapor. The current or conductivity modulation is based on the interfacial charge transfer between the adsorbed explosives molecules and the nanofibril. The interfacial charge transfer results in change of the charge carrier density of the nanofibril. Such current or conductivity modulation of the nanofibril is determined by the pi-pi molecular stacking along the long axis of the nanofibril, and the one-dimensional pi-pi stacking is conducive to the enhancement of the charge migration along the direction of pi-pi stacking.

In one embodiment, the sensing shown in FIG. 1 can also be performed in conjunction with light irradiation of the nanofibrils to create excited state within the nanofibrils, the excited state thus created possessing stronger capability (compared to the ground state) of transfer an electron into the adsorbed explosive molecule. The current or conductivity modulation of the nanofibril (upon exposing the nanofibrils to gaseous molecules, such as explosives vapor) can be enhanced by the photoinduced interfacial charge transfer, providing additional enhancement of the conductivity modulation that is originally caused by the explosive adsorption.

In one embodiment, the sensing shown in FIG. 1 can also be performed in conjunction with gate modulation, which can be performed by applying a voltage bias between the source and gate electrode, the three-electrode device thus fabricated being able to function as a field-effect transistor (FET). Two options are available for increasing the sensing sensitivity: either increasing the current (ION) of the ON state (in exposure to explosives vapor, i.e., with explosives molecules adsorbed on the nanofibril), or decreasing the current (IOFF) of the OFF state (in the absence of explosives adsorption). Decreasing the current (IOFF) of the OFF state can be realized by applying a reverse gate bias, at which the FET operates at depletion mode and produces close-to-zero current (or conductivity) for the bare nanofibril (which is intrinsically dopant free). The close-to-zero background current thus obtained provides increased sensing sensitivity for detecting the adsorption of explosives by monitoring the larger increase in current.

In one embodiment, the sensing shown in FIG. 1 can also be performed in a phototransistor mode, for which the sensing is based on modulation of photocurrent, rather than dark-current, wherein the photocurrent is defined as the electrical current measured under light irradiation, and the dark-current is defined as the current measured in the absence of light irradiation. The sensing sensitivity under phototransistor mode can be increased by operating the device under light irradiation that initiates the efficient photoinduced charge transfer between adsorbed explosives molecules and the nanofibrils, resulting in a dramatic increase in photocurrent at the adsorption state, thus leading to enhancement in current modulation.

Another aspect of the present invention provides the development or synthesis of the molecules that are used as the building blocks to fabricate the nanofibrils. The molecules are of the class of arylene-ethynylene macrocycle (AEM), which consists of a shape-persistent, toroidal scaffold in planar conformation, with minimal ring strain and highly tunable ring sizes (from 0.5 nm to above 5 nm). The developed synthesis enables the preparation of AEM molecules that are highly tunable and adaptable with respect to structure, geometry, size and redox properties, providing enormous options for optimizing the crystalline structure, internal void dimensions and optoelectronic properties (related to both optical and electrical properties) of the nanofibers to achieve the maximal sensitivity in optoelectronic sensing. The molecular structures of the molecules are schematically depicted in FIG. 2.

Figure 2:
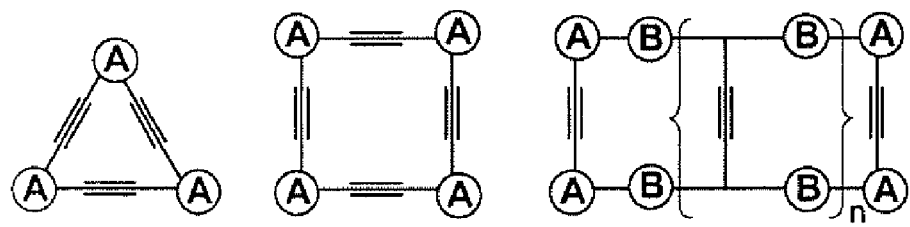
FIG. 2 shows the schematic drawing of the molecules used as building block for fabrication the fluorescent nanofibrils.
Figure 2:
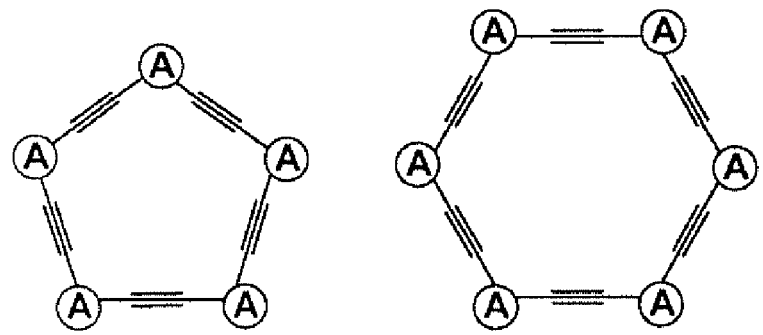

In FIG. 2, A is the corner-joint group; A is designed to have a structure accommodating the backbone frames of triangle, square, pentagon and hexagon, which demand different angles of connection between the edges and the corners; A is also the site to link the side chains, which provide solubility for the molecules; A is designed to afford complete conjugation of the whole backbone frame; A is also designed to afford planar conformation of the whole backbone frame; the molecular structure of A is flexible with regard to modification of functional groups to afford different redox capabilities and intermolecular binding properties, and to afford different sizes of the whole backbone frame, with edge lengths ranging from below 1 nm to above 5 nm, and to afford different electronic structure, resulting in absorption and emission spectra of the molecule covering broad region from ultraviolet to visible, and to afford different options for linking with different structures of side chains, for which the different connection moieties at the backbone may provide different conformation between the side chains and the backbone frame, ranging from co-planar to tilting-out-of-plane, and to afford hydrogen-bonding or any other intermolecular interaction, providing enhancement for the molecular arrangement between the molecules.

In FIG. 2, n can be an integer larger than zero; A is the corner-joint group; the triple solid lines refer to a triple carbon-carbon bond; the single solid line refers to a sigma carbon-carbon bond.

In FIG. 2, B is a functional group and part of the conjugation in the edge of the polygon backbone frame; B is designed to have a structure accommodating the backbone frames of in planar configuration; B can also be the site to link the side chains, which provide solubility for the molecules; B is designed in a way to afford complete conjugation of the whole backbone frame; B is also designed to afford planar conformation of the whole backbone frame; the molecular structure of B is flexible with regard to modification of functional groups to afford different redox capabilities and intermolecular binding properties, and to afford different sizes of the whole backbone frame, with edge lengths ranging from below 1 nm to above 5 nm, and to afford different electronic structure, resulting in absorption and emission spectra of the molecule covering broad region from ultraviolet to visible, and to afford different options for linking with different structures of side chains, for which the different connection moieties at the backbone may provide different conformation between the side chains and the backbone frame, ranging from co-planar to tilting-out-of-plane, and to afford hydrogen-bonding or any other intermolecular interaction, providing enhancement for the molecular arrangement between the molecules.

In FIG. 2, the side chains connected at the A groups can be any chemical groups that provides good solubility for the molecules in solvents, and provides weak steric hindrance for the co-facial stacking between the molecules. The side chains can be connected to the backbone with different chemical moieties, which can be (but not exclusively) —(C=O)—O—, —(C=S)—O—, —(C=O)—, —(C=S)—, which provide co-planar conformation between the backbone frame and the linear side chains.

Figure 3:
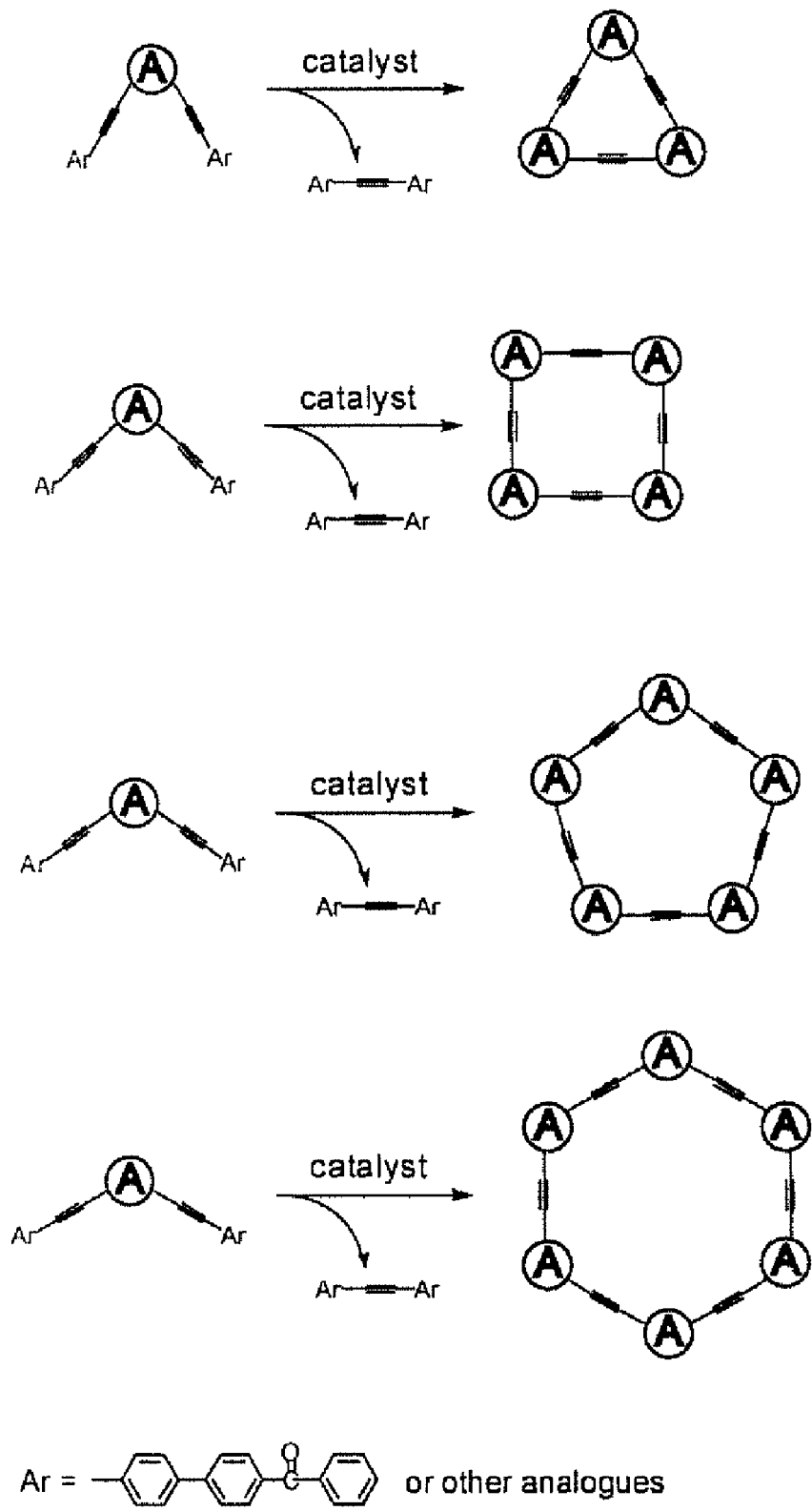
FIG. 3 shows the schematic diagram of the synthesis of the building block molecules in polygon.

In one embodiment, the synthesis of the molecules depicted in FIG. 2 can be performed via the precipitation-driven cyclooligomerization of the precursors as shown in FIG. 3, where Ar can be any protection group that is suited for the reaction; the triple solid lines refer to a triple carbon-carbon bond; the single solid line refers to a sigma carbon-carbon bond.

Figure 4:
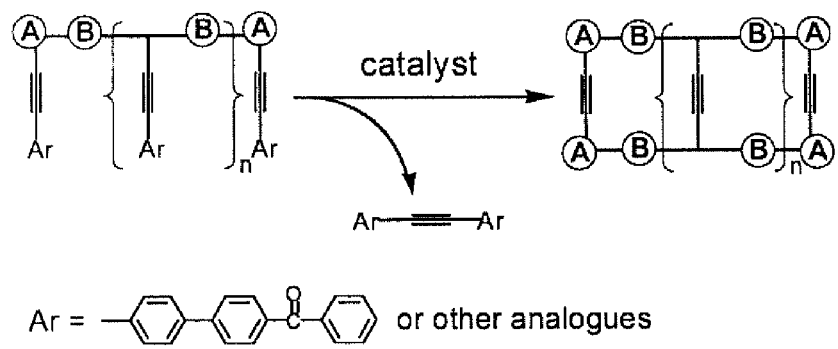
FIG. 4 shows the schematic diagram of the synthesis of the building block molecules in ladder shape.

In one embodiment, the synthesis of the ladder-like molecule depicted in FIG. 2 can be synthesized via the precipitation-driven cyclooligomerization of the precursors as shown in FIG. 4, where Ar can be any protection group that is suited for the reaction; the triple solid lines refer to a triple carbon-carbon bond; the single solid line refers to a sigma carbon-carbon bond.

Figure 5:
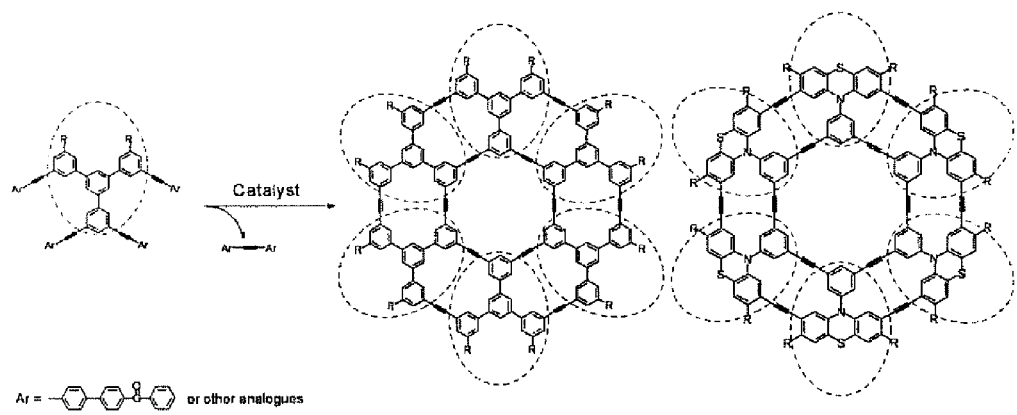
FIG. 5 shows schematic diagram of the synthesis of the net-like building block molecules.

In one embodiment, the precursors used for the synthesis shown in FIG. 3 can be made with more than two coupling sites (i.e., the -°-Ar sites), particularly 3, 4, 5 or more coupling sites depending on the synthesis of the molecules with specific molecular structures. By using a precursor with more than two coupling sites (i.e., the -°-Ar sites), a net-like molecule can be synthesized from the precursors. FIG. 5 shows a typical example, where a precursor modified with 4 coupling sites (i.e., the -°-Ar sites) is used.

In FIG. 5, R can be any chemical groups that are suited to provide the whole molecule with good solubility; Ar can be any protection group that is suited for the reaction; the triple solid lines refer to a triple carbon-carbon bond; the single solid line refers to a sigma carbon-carbon bond.

In one embodiment, the group circled in the dotted line (shown in FIG. 5) can be any chemical group as defined as A in FIG. 3; the reducing capability and electronic structure of the whole conjugated molecule can thus be adjusted by incorporation of reducing chemical moieties including sulfur, nitrogen, oxygen or any other chemical unit.

Another aspect of the present invention provides a sensor and a method for sensing the vapor of the explosives (such as TNT and DNT) and other volatile organic compounds, including the explosives taggants through the modulation of the fluorescence of the nanofibril film and the electrical conductivity of the nanofibrils.

Another aspect of the present invention provides an approach to optimization of the one-dimensional molecular arrangement along the long axis of the nanofibril; organized one-dimensional molecular arrangement is highly favorable for exciton (excited state) migration (via intermolecular electronic coupling) and charge transport (via pi-electronic delocalization). The long-range exciton migration and charge transport intrinsic to the nanofiber enable development of multimode optoelectronic sensors that demand both amplified fluorescence quenching and large modulation of electrical current by surface adsorption of molecules that are of interest of detection.

Another aspect of the present invention provides an approach to combine the porous properties of the nanofibril film with the extended exciton migration intrinsic to the individual nanofibers, making the nanofibril film an efficient sensing material for detecting oxidative volatile organic compounds (VOCs), particularly explosives.

Another aspect of the present invention demonstrates that the nanofibril sensors thus described above showed ideal persistence against the potential interference from the common environmental backgrounds, including (but no exclusively) various liquids (e.g., water, alcohols, gasoline, acetone, etc.), cosmetics (e.g., perfumes, creams, shampoo, hair spray, etc.) and. The sensing persistence (selectivity) has also examined by testing the nanofibril sensor in some extreme cases, such as exposure closely to a car exhaust pipe and heavy personal smoking, showing no influence on the sensing from $CO_2$ and the nitrogen oxide gases. In all these cases, no significant fluorescence quenching has been observed, whereas for the same film more than 60% quenching was obtained upon exposure to 5 ppb TNT.

The function and advantage of these and other embodiments of the present invention will be more fully understood from the examples below. The following examples are intended to illustrate the certain embodiments of the present invention, but do not exemplify the full scope of the invention.

EXAMPLES

Example 1

Figure 6:
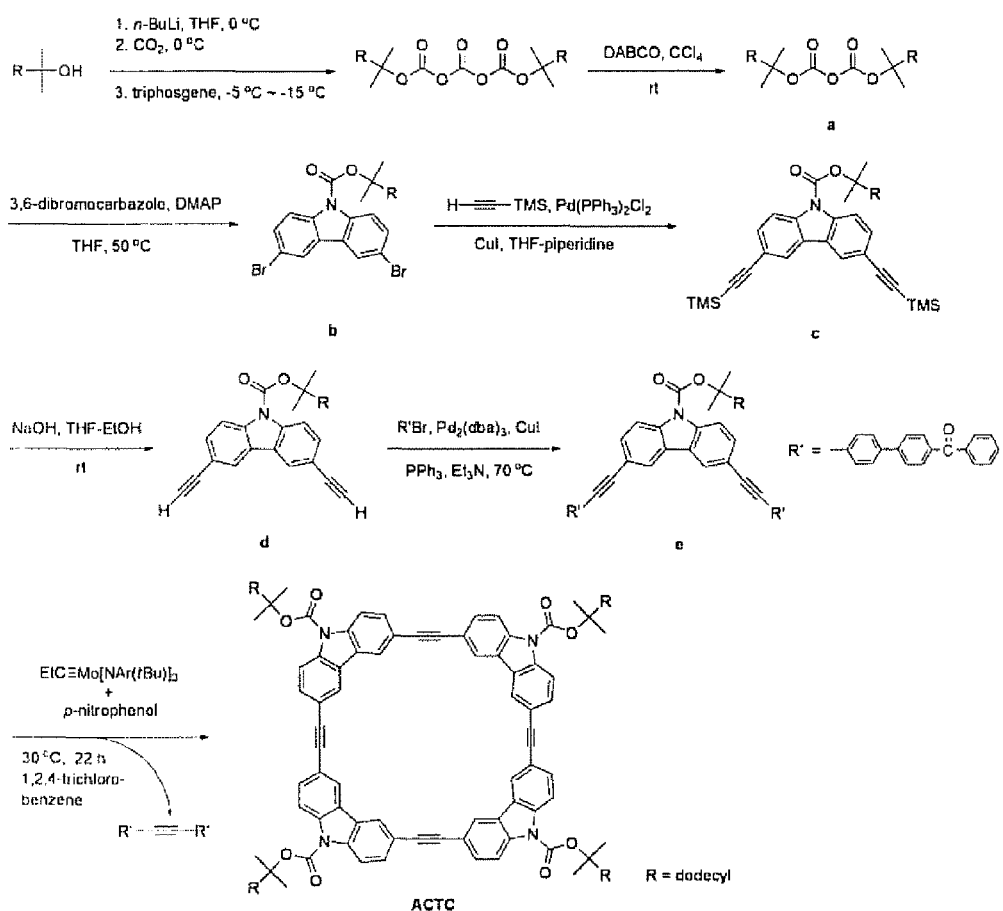
FIG. 6 shows the details of the synthesis of an ACTC molecule.
Figure 7:
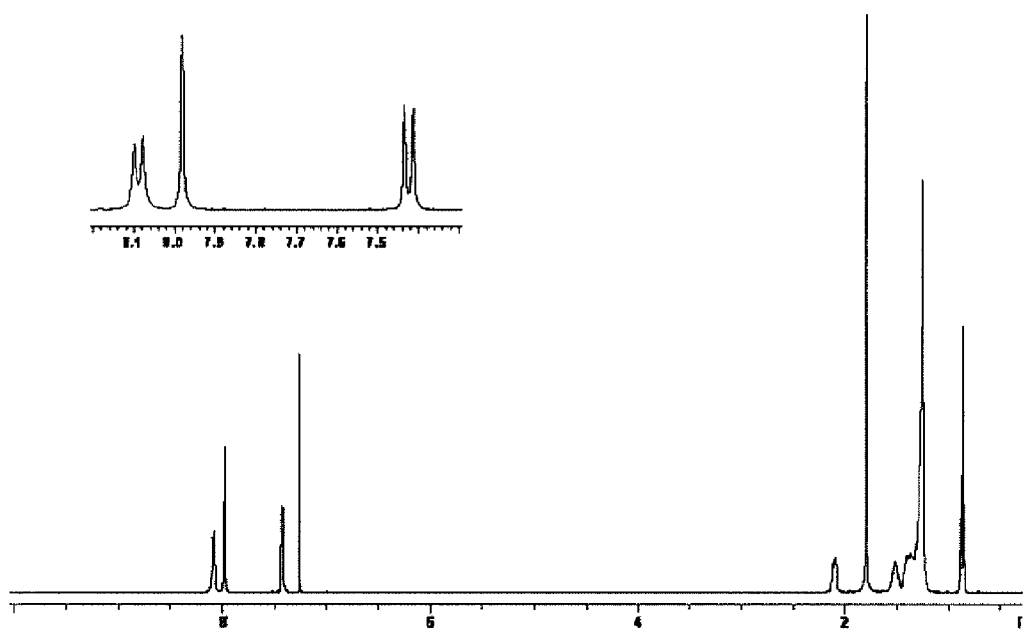
FIG. 7 shows 1H NMR spectrum of ACTC (CDCl3, 500 MHz, 40° C.)
Figure 8:
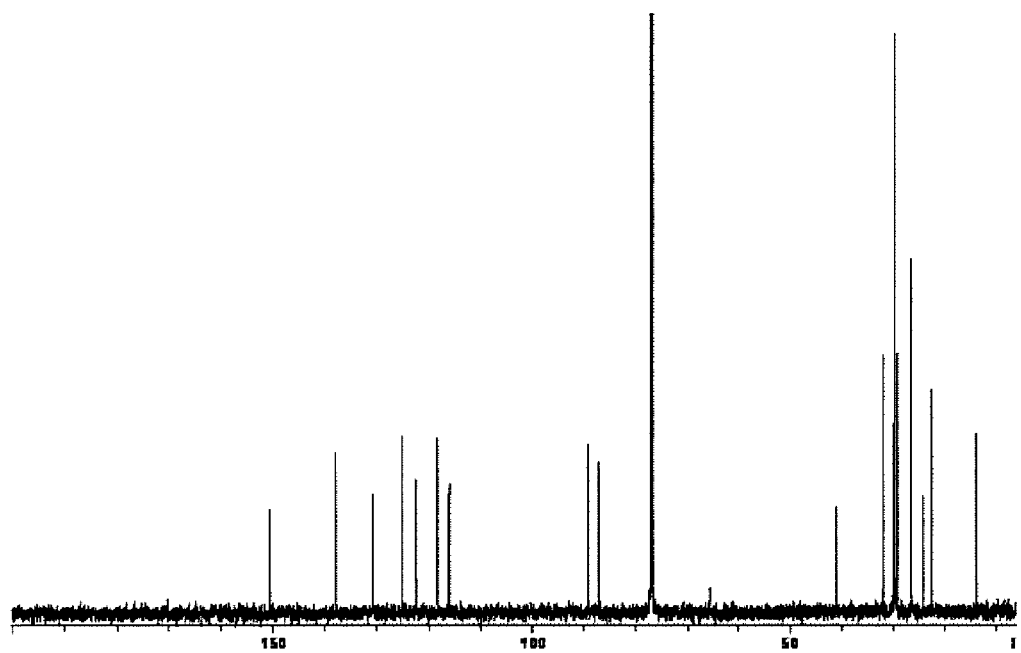
FIG. 8 shows 13C NMR spectrum of ACTC (CDCl3, 125 MHz, 40° C.)
Figure 9:
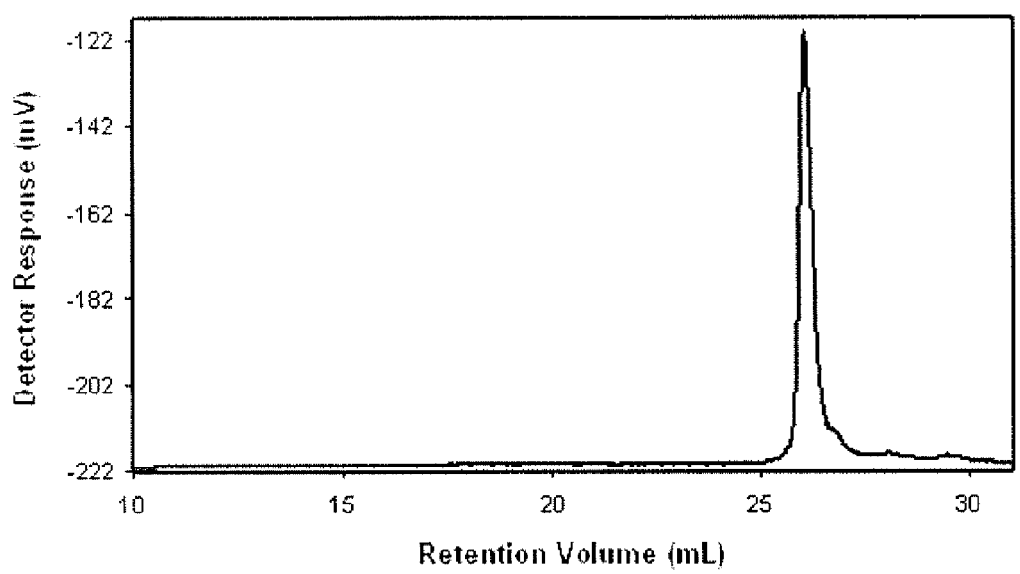
FIG. 9 shows GPC trace of ACTC (THF, 25° C.)

Synthesis of an AEM Molecule in Square Shape, Named ACTC as Shown in FIG. 6

ACTC was synthesized following the protocol depicted in FIG. 6. All air or moisture-sensitive manipulations were performed under argon protection using standard Schlenk techniques or in an argon filled glove box (model TS-5000 from Vacuum/Atmospheres Company). $CCl_4$ was distilled over $P_2O_5$ and degassed before use. THF was distilled over Na before use. Analytical thin-layer chromatography (TLC) was performed on Kieselgel F-254 precoated silica gel plates. Visualization was performed with UV light (254 nm) or iodine stain. Flash column chromatography was conducted with silica gel 60 (230-400 mesh, 60 Å) from EM science.

The 1H and 13C NMR spectra were recorded on 400 or 500 MHz NMR spectrometers in School of Chemical Science (SCS) VOICE NMR Laboratory at the University of Illinois (http://www.scs.uiuc.edu/~mainzv/VOICE_NMR_Lab/). Proton chemical shifts are expressed in parts per million ($\delta$) using the residual solvent protons as an internal standard. Carbon-13 chemical shifts are also expressed in parts per million ($\delta$) using the solvent's 13C resonance as an internal standard. Coupling constants (J) are reported in Hertz (Hz), and splitting patterns are designated as s (singlet), d (doublet), t (triplet), q (quartet), m (multiplet) and br (broad). Low and high resolution EI, FAB and MALDI mass spectra were obtained in the SCS Mass Spectrometry Facility at the University of Illinois. Elemental analyses were performed by the University of Illinois Micro Analytical Service Laboratory. Gel permeation chromatography (GPC) measurements were performed in THF at 25° C. with a Waters 515 HPLC pump, Viscotek TDA model 300 triple detector, and a series of three Viscogel 7.8×300 mm columns (two GMHXL16141 columns and one G3000HXL16136 column). Molecular weight data were determined using Viscotek's TriSEC software.

Bis(1,1-dimethyltridecyl)dicarbonate (a): To a solution of 2-methyl-2-tetradecanol (7.16 g, 31.4 mmol) in THF (44 mL) at 0° C. was added n-BuLi (1.6 M in hexane, 19.7 mL) dropwise within 10 min. The mixture was stirred for 40 min during which time it was allowed to warm up to room temperature. Then the solution was cooled down to −5° C. ~−15° C. in an ice-salt bath and a stream of anhydrous $CO_2$ was passed through the cold reaction solution for 45 min. When the addition of $CO_2$ is complete, a solution of triphosgene (2.34 g, 7.90 mmol) in benzene (7.0 mL) was added to the cold reaction mixture dropwise and with vigorous stirring over 20 min, maintaining the temperature of the cooling bath at −5° C. ~−15° C. When the addition of the triphosgene solution was complete, the cold reaction mixture was stirred for additional 40 min while a stream of anhydrous $N_2$ was passed through. The solvent was then removed in vacuo. To the residue was added $CCl_4$ (40 mL) at room temperature, followed by addition of DABCO (0.043 g, 0.39 mmol), resulting in evolution of $CO_2$. The reaction mixture was stirred at room temperature for 45 min before an aqueous citric acid solution (20 mL, pH 5~6) was added. The organic layer was separated, dried over $MgSO_4$ and concentrated in vacuo at 25° C. The residue was purified by column chromatography (n-hexane) affording the product as colorless oil (5.61 g, 68%). 1H NMR ($CDCl_3$, 500 MHz): d 1.78 (m, 4H), 1.52 (s, 12H), 1.22-1.36 (m, 40H), 0.88 (t, J=6.7 Hz, 6H); 13C NMR ($CDCl_3$, 125 MHz): δ 146.7, 89.8, 40.2, 31.9, 29.6 (br, signal overlap), 29.3, 25.2, 22.7, 14.1.

3,6-Dibromocarbazole-9-carboxylic acid 1,1-dimethyltridecyl ester (b): To a solution of 3,6-dibromocarbazole (4.28 g, 13.2 mmol) and 4-N,N-dimethylaminopyridine (DMAP) (0.307 g, 2.51 mmol) in THF (35 mL) was added dicarbonate a (6.60 g, 12.6 mmol) via syringe dropwise at room temperature. The resulting mixture was heated at 50° C. for 4 h, followed by addition of diethyl ether (50 mL) to the cooled solution. The organic layer was washed with $H_2O$ (20 mL) and brine (20 mL), dried over $MgSO_4$ and concentrated in vacuo. The residue was purified by column chromatography (n-hexane) affording the product as light yellow oil (6.82 g, 94%). 1H NMR ($CDCl_3$, 500 MHz): d 8.14 (d, J=8.6 Hz, 2H), 8.02 (d, J=1.7 Hz, 2H), 7.56 (dd, J=8.6, 1.8 Hz, 2H), 2.04 [m, 2H, OC(CH3)2CH2(CH2)10CH3], 1.72 [s, 6H, OC(CH3)2CH2(CH2)10CH3], 1.22-1.46 (m, 20H, OC(CH3)2CH2(CH2)10CH3], 0.88 (t, J=6.8 Hz, 3H, OC(CH3)2CH2(CH2)10CH3]; 13C NMR ($CDCl_3$, 125 MHz): δ 150.4 (NCOO), 137.5, 130.5, 126.2, 122.6, 117.8, 116.3, 87.4 [OC(CH3)2CH2(CH2)5CH3], 40.5, 31.9, 29.8, 29.6 (br, signal overlap), 29.5, 29.4, 29.3, 26.3, 24.0, 22.7, 14.1; MS (EI): m/z (%): 579.2 (3), 482.8 (6), 425.0 (16), 368.9 (17), 324.9 (100), 244.0 (24), 210.3 (14), 164.1 (27), 82.9 (30); HR-MS (C28H37Br2NO2): calcd 577.1212, found 577.1204; TLC Rf=0.26 (n-Hexane).

3,6-Bis(trimethylsilylethynyl)carbazole-9-carboxylic acid 1,1-dimethyltridecyl ester (c): Application of Sonogashira's general procedure for alkyne coupling [b (3.80 g, 6.56 mmol), trimethylsilylacetylene (6.45 g, 65.6 mmol), Pd(PPh3)2Cl2 (0.276 g, 0.394 mmol), CuI (0.0249 g, 0.131 mmol) in piperidine (10 mL) and THF (18 mL)] gave the product as yellow oil (3.95 g, 98%). 1H NMR ($CDCl_3$, 500 MHz): d 8.19 (d, J=8.6 Hz, 2H), 8.08 (d, J=1.6 Hz, 2H), 7.57 (dd, J=8.8, 1.6 Hz, 2H), 2.04 [m, 2H, OC(CH3)2CH2(CH2)10CH3], 1.71 [s, 6H, OC(CH3)2CH2(CH2)10CH3], 1.23-1.46 (m, 20H, OC(CH3)2CH2(CH2)10CH3], 0.88 (t, J=6.8 Hz, 3H, OC(CH3)2CH2(CH2)5CH3], 0.29 [s, 18H, Si(CH3)3]; 13C NMR ($CDCl_3$, 125 MHz): δ 150.5 (NCOO), 138.5, 131.2, 125.0, 123.6, 117.9, 116.1, 105.2 [ArCCSi(CH3)3], 93.5 [ArCCSi(CH3)3], 87.3 [OC(CH3)2CH2(CH2)5CH3], 40.6, 31.8, 29.8, 29.6 (br, signal overlap), 29.5, 29.4, 29.3, 26.3, 24.0, 22.7, 14.1, −0.01 [Si(CH3)3]; MS (EI): m/z (%): 613.4 (6), 551.3 (12), 490.3 (11), 403.2 (60), 359.2 (100), 344.2 (86), 277.1 (19), 164.7 (43), 129.1 (49), 85.1 (38); HR-MS (C38H55Si2NO2): calcd 613.3771, found 613.3771; TLC Rf=0.24 (CH2Cl2/n-Hexane 1/9).

3,6-Diethynylcarbazole-9-carboxylic acid 1,1-dimethyltridecyl ester (d): To a solution of c (3.94 g, 6.42 mmol), in THF (50 mL) and ethanol (200 mL) at room temperature was added a solution of sodium hydroxide (0.521 g, 13.0 mmol) in $H_2O$ (7.0 mL) dropwise within 10 min. The resulting mixture was stirred at room temperature for 45 min. After removing the solvent in vacuo, the residue was redissolved in $CH_2Cl_2$ (200 mL). The organic layer was washed with $H_2O$ (60 mL) and brine (60 mL), dried over $MgSO_4$ and concentrated in vacuo. The residue was purified by column chromatography (CH2Cl2/n-Hexane 1/9) affording the product as light yellow oil (2.98 g, 99%). 1H NMR ($CDCl_3$, 500 MHz): d 8.22 (d, J=8.6 Hz, 2H), 8.10 (d, J=1.6 Hz, 2H), 7.60 (dd, J=8.7, 1.6 Hz, 2H), 3.12 (s, 2H, ArCCH), 2.04 [m, 2H, OC(CH3)2CH2 (CH2)10CH3], 1.72 [s, 6H, OC(CH3)2CH2(CH2)10CH3], 1.22-1.46 (m, 20H, OC(CH3)2CH2(CH2)10CH3], 0.87 (t, J=6.8 Hz, 3H, OC(CH3)2CH2(CH2)10CH3]; 13C NMR ($CDCl_3$, 125 MHz): δ 150.5 (NCOO), 138.7, 131.4, 125.0, 123.7, 116.9, 116.3, 87.4 [OC(CH3)2CH2(CH2)5CH3], 83.7 [ArCCSi(CH3)3], 76.7 [ArCCSi(CH3)3], 40.5, 31.9, 29.8, 29.6 (br, signal overlap), 29.5, 29.4, 29.3, 26.3, 24.0, 22.7, 14.1; MS (EI): m/z (%): 469.4 (2), 277.1 (8), 259.1 (10), 215.1 (100), 187.1 (8), 129.1 (43), 107.6 (11), 85.1 (27); HR-MS (C32H39NO2): calcd 469.2954, found 469.2959; TLC Rf=0.50 (EtOAc/n-Hexane 1/19).

3,6-Bis(benzoylbiphenyl)ethynylcarbazole-9-carboxylic acid 1,1-dimethyltridecyl ester (e): Application of Sonogashira's general procedure for alkyne coupling [d (2.98 g, 6.34 mmol), 4-benzoyl-4'-bromobiphenyl (4.49 g, 13.3 mmol), Pd2(dba)3 (0.351 g, 0.380 mmol), CuI (0.0241 g, 0.127 mmol), PPh3 (0.669 g, 2.54 mmol) in Et3N (17.0 mL) and DMF (32 mL)] gave the product as a yellow solid (4.29 g, 69%). 1H NMR ($CDCl_3$, 400 MHz): d 8.29 (d, J=8.6 Hz, 2H), 8.21 (d, J=1.8 Hz, 2H), 7.92 (d, J=8.8 Hz, 4H), 7.85 (m, 4H), 7.74 (d, J=8.7 Hz, 4H), 7.67-7.71 (m, 10H), 7.61 (m, 2H), 7.52 (m, 4H), 2.07 μm, 2H, OC(CH3)2CH2(CH2)10CH3], 1.75 [s, 6H, OC(CH3)2CH2(CH2)10CH3], 1.23-1.51 (m, 20H, OC(CH3)2CH2(CH2)10CH3], 0.87 (t, J=6.6 Hz, 3H, OC(CH3)2CH2(CH2)10CH3]; 13C NMR ($CDCl_3$, 100 MHz): δ 196.3 (ArCOAr), 150.5 (NCOO), 144.3, 139.5, 138.5, 137.6, 136.5, 132.4, 132.2, 131.0, 130.8, 130.0, 128.3, 127.2, 126.8, 125.2, 123.3, 123.1, 117.9, 116.4, 90.9 [ArC-CAr], 88.6 [ArCCAr], 87.4 [OC(CH3)2CH2(CH2)5CH3], 40.6, 31.9, 29.9, 29.6 (br, signal overlap), 29.5, 29.4, 29.3, 26.4, 24.1, 22.7, 14.1; MS (FAB): m/z (%): 982.5 (2), 772.2 (5), 460.1 (3), 307.1 (29), 154.1 (100); HR-MS (C70H63NO4): calcd 982.4835, found 982.4839; TLC Rf=0.18 (CH2Cl2/n-Hexane 4/1); Anal. Calcd for C65H53NO4 (912.4): C, 85.59; H, 6.46; N, 1.43; Found: C, 85.67; H, 6.39; N, 1.66.

ACTC: In an argon filled glove box, a solution of molybdenum triamide (67.9 mg, 0.102 mmol) and p-nitrophenol (42.5 mg, 0.305 mmol) in 1,2,4-trichlorobenzene (14 mL, anhydrous grade) was added to a solution of monomer e (1.00 g, 1.02 mmol) in 1,2,4-trichlorobenzene (28 mL). The flask was sealed and removed from the glove box. The resulting mixture was stirred for 22 h at 30° C. After removal of the precipitate by vacuum filtration, the solvent was removed by distillation under high vacuum (50° C., 1 mmHg). CH2Cl2 (15 mL) was added to the residue and the resulting mixture was stirred vigorously until the product became fine particles. After filtration, the product was washed with CH2Cl2 (3×5 mL) to give ACTC macrocycle as a white solid (0.366 g, 81%). 1H NMR (CDCl3, 500 MHz): d 8.10 (d, J=8.6 Hz, 8H), 8.00 (s, 8H), 7.44 (d, J=8.6 Hz, 8H), 2.11 [m, 8H, OC(CH3)2CH2(CH2)10CH3], 1.80 [s, 24H, OC(CH3)2CH2(CH2)10CH3], 1.23-1.54 (m, 80H, OC(CH3)2CH2(CH2)10CH3], 0.87 (t, J=6.6 Hz, 12H, OC(CH3)2CH2(CH2)10CH3]; 13C NMR (CDCl3, 125 MHz): δ 150.5 (NCOO), 138.0, 130.7, 125.1, 122.4, 118.2, 116.0, 89.1 [ArCCAr], 87.0 [OC(CH3)2CH2(CH2)5CH3], 40.8, 31.9, 30.0, 29.7 (br, signal overlap), 29.6, 29.5, 29.4, 26.4, 24.2, 22.7, 14.1; MS (FD): m/z (%): 1773.3 (21), 887.0 (100), 525.3 (66); Anal. Calcd for C120H148N4O8 (1773.1): C, 81.22; H, 8.41; N, 3.16; Found: C, 80.93; H, 8.05; N, 3.24; GPC 2030 (Mn), 1.02 (Mw/Mn).

Example 2

Figure 10:
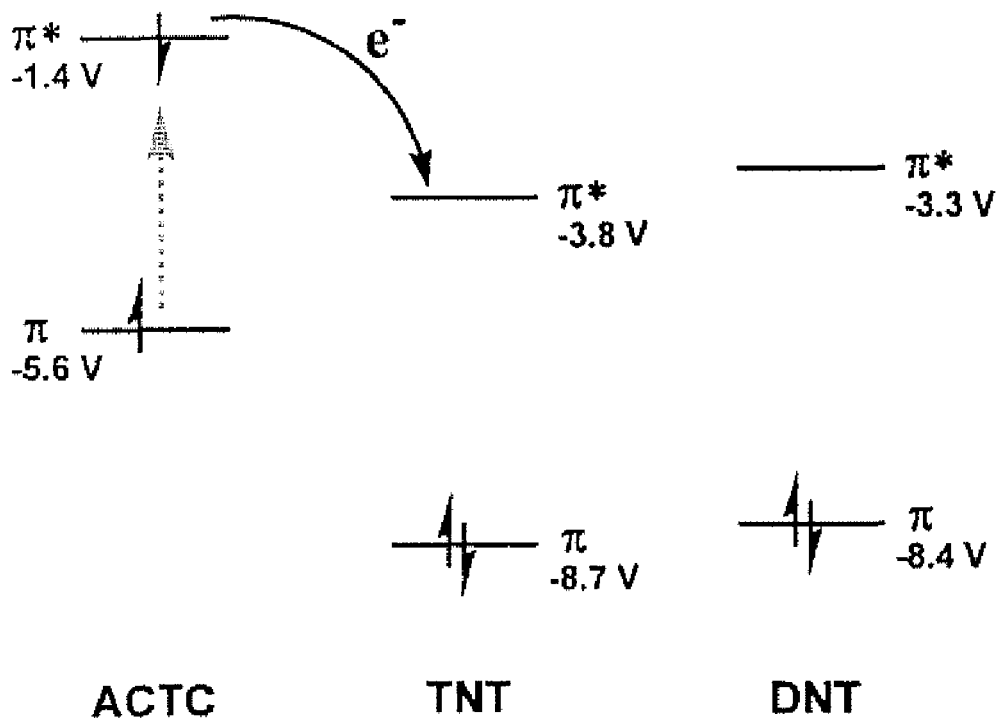
FIG. 10 shows energy levels of HOMO (pi) and LUMO (pi*) orbitals of ACTC, TNT and DNT.
Figure 11:
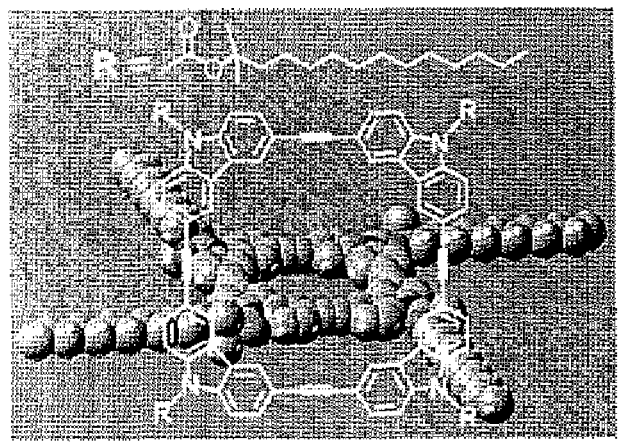
FIG. 11 shows Molecular structure of ACTC.

Theoretical Calculation of Energy Levels of HOMO (Pi) and LUMO (Pi*) Orbitals of ACTC, TNT and DNT, and the Molecular Configuration of ACTC The results show a planar configuration of ACTC (FIG. 10), and large driving force of electron transfer from the photoexcited state of ACTC to TNT (2.4 eV) and DNT (1.9 eV) as shown in FIG. 11. Geometry optimization and energy calculation were performed with density-functional theory (B3LYP/6-31 g*) using Gaussian 03 package.

Example 3

Fabrication and Microscopy Characterization of ACTC Films

Figure 12:
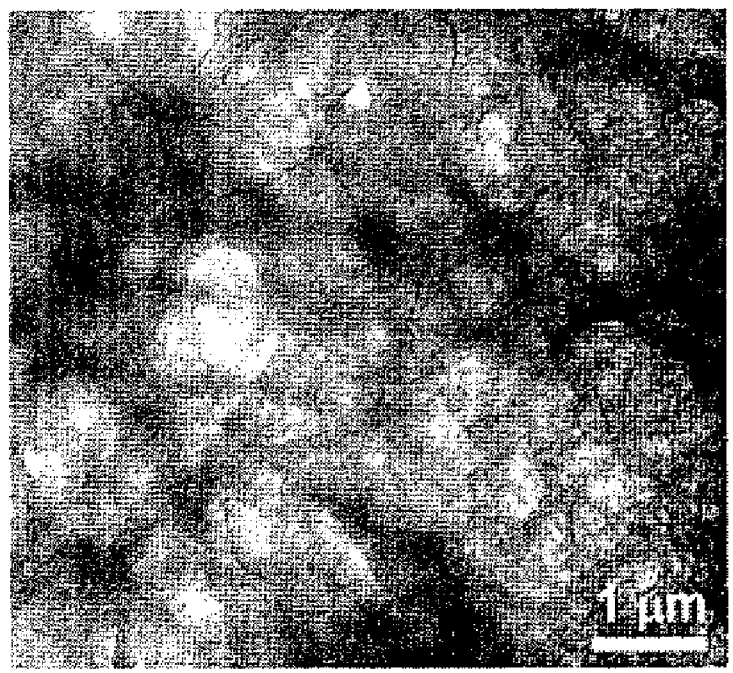
FIG. 12 shows TEM image of a thin film of ACTC cast on silicon oxide from 2 mM THF solution.
Figure 13:
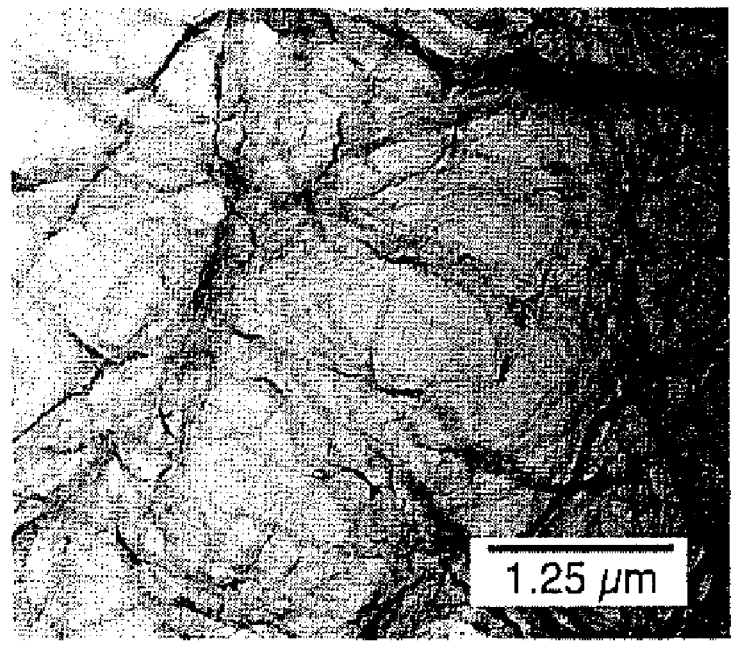
FIG. 13 shows TEM image of ACTC nanofibrils formed by casting a small amount of THF solution (2 mM) onto a holey carbon grid, for which a filter paper was used as the substrate to drain the excessive solution.

A uniform film of ACTC was fabricated by spin-casting one drop of the ACTC solution in THF onto a glass cover slip at a speed of 1,500 rpm. By changing the concentration of the ACTC solution (0.2-1.0 mM), different thickness of films were obtained as characterized below with AFM and spectroscopy methods. The rigid, planar geometry of the ACTC molecule (including both core and the side chains) affords effective cofacial stacking between molecules, leading to formation of one-dimensional, fibril nanostructures (FIG. 12 and FIG. 13). Indeed, the long nanofibril structures shown in FIG. 13 were fabricated simply by depositing a small amount of THF solution of ACTC (2 mM) onto a carbon grid. The long-range molecular stacking is conducive to the pi-pi electronic interaction along the long-axis, thus resulting in efficient exciton migration along the fiber. Moreover, entangled piling of large number of the nanofibrils produces extensively porous structure and large surface area of the film, which are both conducive for increasing the adsorption of explosives molecules.

Example 4

Optical Spectroscopic Characterization of Molecules and Films

Figure 14:
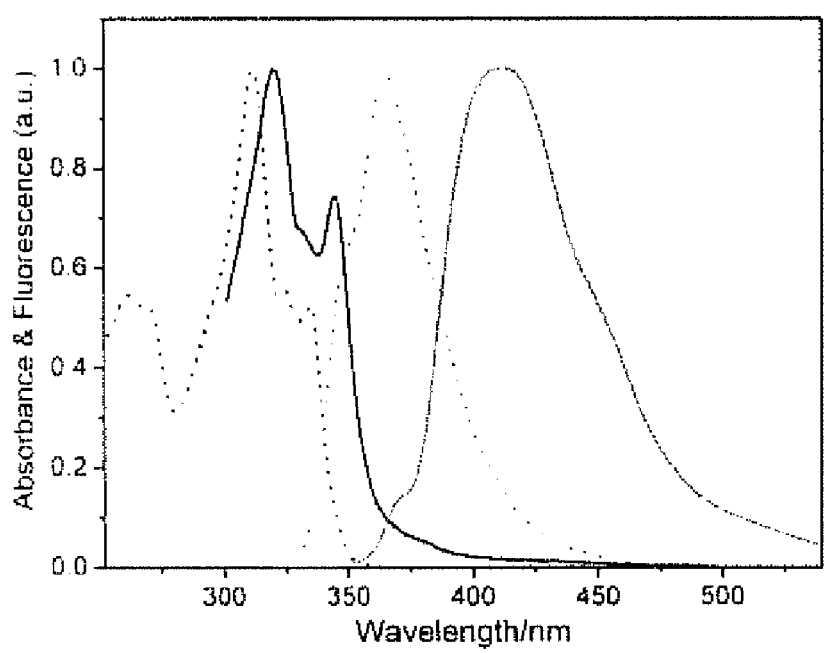
FIG. 14 shows absorption (black) and fluorescence (red) spectra of molecularly dissolved solution (dotted) and drop-cast film (solid) of ACTC. The solution used for spectral measurement was 1 micro-M of ACTC dissolved in THF. The film was cast from a 2 mM THF solution of ACTC. All spectra normalized to the maxima.

FIG. 14 shows the absorption and fluorescence spectra of ACTC in both solutions and solid state. ACTC dissolved in a solution is highly fluorescent, with quantum yield of 0.7 (calibrated with pyrene dissolved in cyclohexane, with yield of 0.32). Upon aggregate (molecular stacking), the strong pi-pi interaction (i.e. electronic coupling) between molecules shifts the emission band to longer wavelength by about 70 nm. Consistent with the emission spectral change, the absorption transition around 340 nm is relatively enhanced upon molecular stacking. These spectral changes are characteristic of pi-pi stacked molecular aggregate, for which like an excimer, the collective electronic features are significantly different from the individual component molecules. The fluorescence quantum yield of the ACTC film (ca. 0.19) was also estimated by calibration with pyrene solution in cyclohexane, with yield of 0.32.

Figure 15:
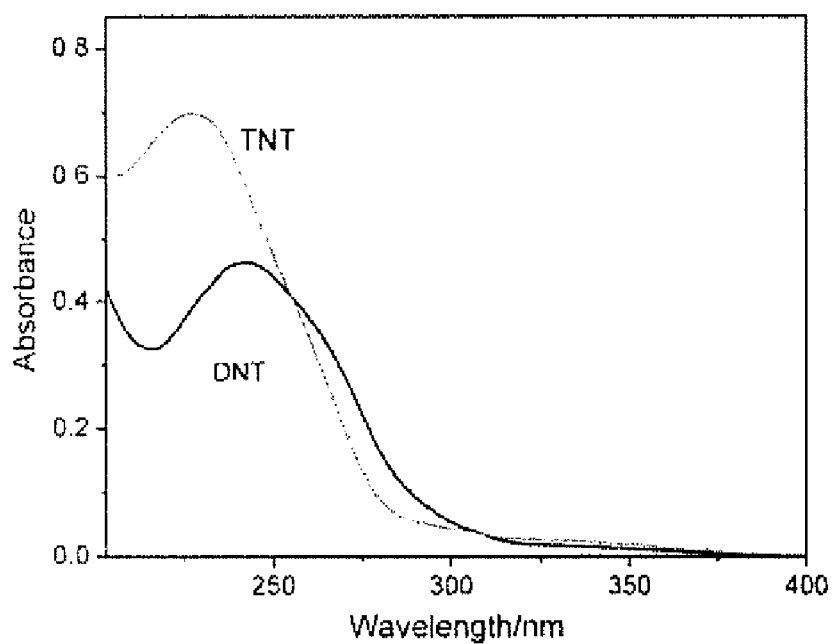
FIG. 15 shows Absorption spectra of DNT (black) and TNT (red) dissolved in methanol at a concentration of 50 micro-M.

FIG. 15 shows the absorption spectra of DNT and TNT molecules. Apparently, both molecules absorb irradiation below 300 nm. In comparison, the emission of ACTC film is far above 350 nm as shown in FIG. 14. The lack of overlap between the ACTC emission and the absorption of DNT and TNT excludes the probability of energy transfer from the excited ACTC to the explosives quencher. Thereby, the effective fluorescence quenching observed in this study is solely due to the photoinduced electron transfer from the singlet state of ACTC to the ground state of the quencher. Such a charge transfer process is consistent with the strong oxidation potential of DNT and TNT, as previously evidenced in the fluorescence quenching of conjugate polymers.

Our ab initio calculation shows that the driving force of the photoinduced electron transfer between ACTC molecule and the quencher is as large as 2.4 and 1.9 eV for TNT and DNT, respectively (FIG. 10). Such large driving force ensures efficient electron transfer, and thus fluorescence quenching. The larger driving force for TNT implies a stronger quenching efficiency compared to DNT, as indeed observed in this study, i.e. comparable quenching was obtained for TNT (83%) and DNT (90) at adsorption equilibrium, whereas the vapor pressures of the two quenchers are different by as large as 20 times, 100 ppb for DNT and only 5 ppb for TNT. Upon molecular stacking in solid state, the LUMO level of ACTC decreases only about 0.1 eV based on the shift of absorption band shown in FIG. 14. Such slight decrease does not affect significantly the electron transfer process indicated in FIG. 10.

Example 5

Calibration of Film Thickness Via AFM and Optical Spectrometry

Figure 16:
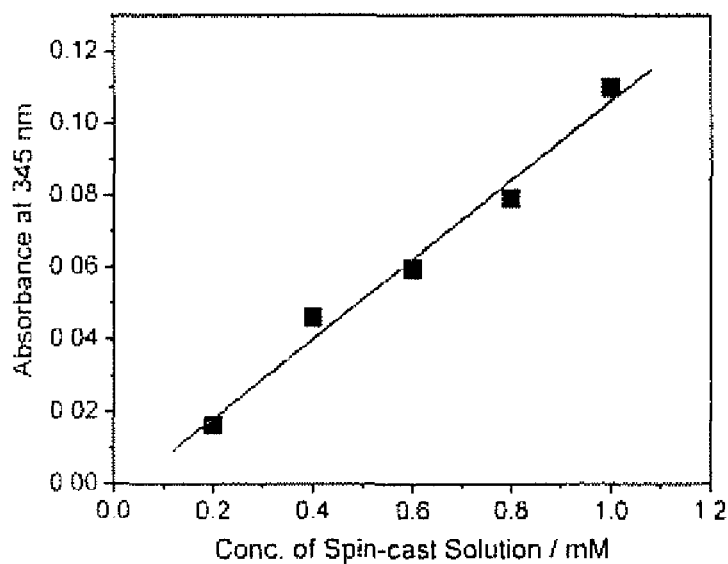
FIG. 16 shows Dependence of absorption of ACTC film at 345 nm (the maximum at long wavelength) on the concentration of the casting solution.
Figure 17:
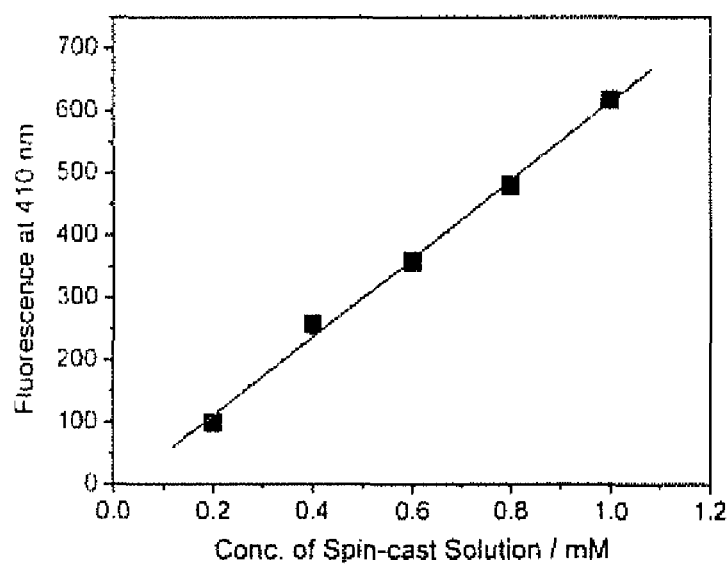
FIG. 17 shows Dependence of fluorescence intensity of ACTC film at 410 nm (the maximum) on the concentration of the casting solution.

Films of various thicknesses were fabricated by spin-casting different concentrations of the ACTC solution in THF, ranging from 0.2 mM to 1.0 mM. As expected, the absorbance of the film is linearly proportional to the concentration of the casting solution (FIG. 16). Since the absorbance is proportional to the film thickness (Beer's law), the calibration data shown in FIG. 16 demonstrates linear dependence of film thickness on the concentration of casting solution. Due to the low absorbance (and thus minimal self-absorption of the fluorescence) of the film within this thickness range, the same linear dependence was also observed for the fluorescence intensity measured for the film, as shown in FIG. 17. The calibration ratios (the slope of the linear fitting shown in FIGS. S8 and S9 after normalization) obtained for the UV-vis absorption and fluorescence measurements are remarkably consistent, with values of 1.0±0.08 and 1.02±0.04, respectively. With such spectrometry calibration, we could estimate the thickness of all the films based on AFM measurement of one of the films. Here, we measured the thickness of the thinnest film with tapping mode AFM, and obtained an average thickness of 18 nm. Based on this value, the thicknesses of other four films (shown in FIGS. 16 and 17) were deduced from the linear calibration curve: 36, 54, 72, 90 nm.

Example 6

Quenching of Fluorescence of ACTC Film Upon Exposure to TNT and DNT Vapor

The fluorescence quenching by DNT and TNT was monitored as follows. Briefly, the fluorescence spectra of the nanofibril film were measured immediately after immersing inside a sealed-jar (50 mL) containing small amount of the explosives (TNT or DNT). To prevent direct contact of the film with the explosives analytes, some cotton was used to cover the explosives powder deposited at the bottom of the jar. Before use the jar was sealed for overnight to achieve constant, saturated vapor pressure inside. The presence of cotton also helps maintain a constant vapor pressure.

Figure 18:
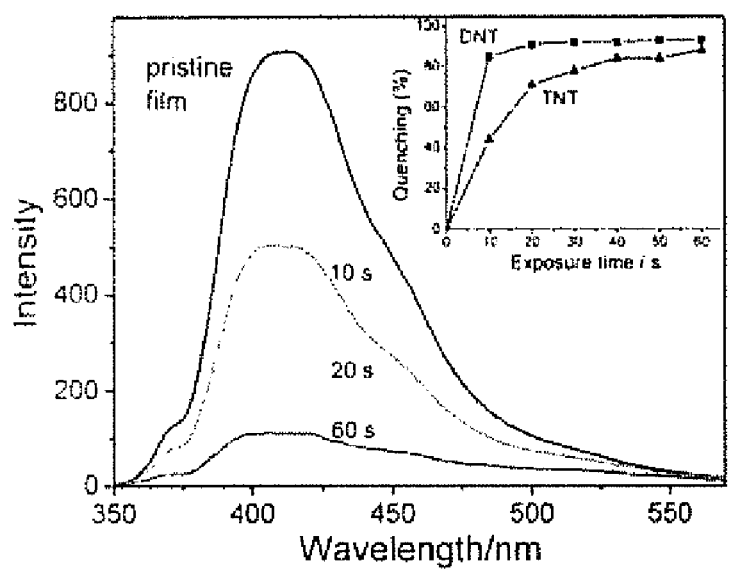
FIG. 18 shows Fluorescence spectra of a 90 nm thick ACTC film upon exposure to saturated vapor of TNT (5 ppb) at different times. Inset: time-course of quenching for TNT and DNT.
Figure 19:
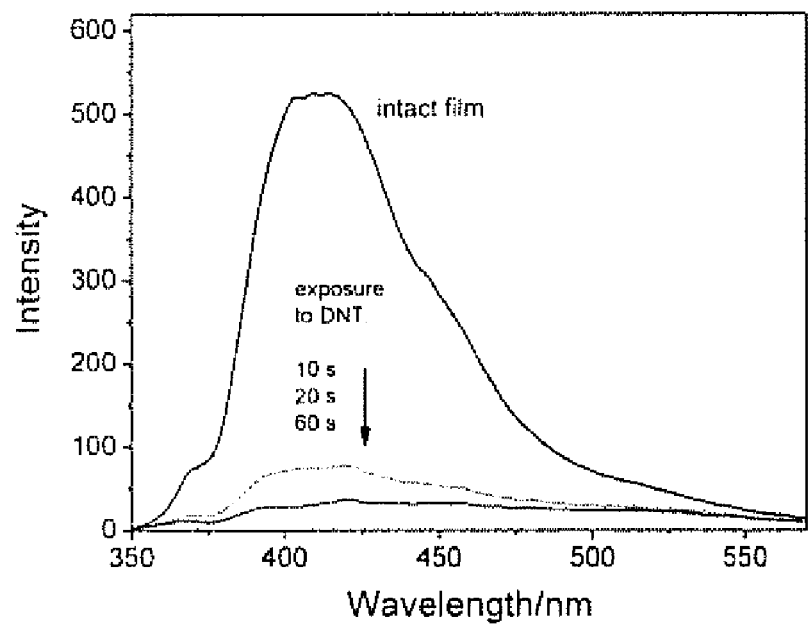
FIG. 19 shows Fluorescence spectra of a 90 nm ACTC film upon exposure to saturated vapor of DNT (100 ppb) at different times.

The ACTC film thus fabricated in Example 3 is quite fluorescent, with quantum yield ca. 0.19. Upon exposure to saturated vapor of DNT or TNT, the fluorescence of the ACTC film was dramatically quenched (FIGS. 18 and 19). Since the emission wavelength of ACTC is far above the absorption range of the two explosives (FIGS. 14-15), and thus there is no possibility for excited state energy transfer, the observed fluorescence quenching must explicitly be due to the photoinduced electron transfer from the excited ACTC to the quencher. Such a photoinduced electron transfer is highly favored by the large driving forces (2.4 eV and 1.9 eV for TNT and DNT, respectively, FIG. 10).

As shown in the inset of FIG. 18, the quenching response to DNT is faster than that to TNT, likely due to the higher vapor concentration of DNT (ca. 100 ppb, compared to ca. 5 ppb of TNT). The fluorescence quenching eventually saturated for both explosives upon reaching the adsorption equilibrium. It is remarkable to note that at adsorption equilibrium (after ca. 60s of exposure) the quenching efficiency of TNT (83%) was comparable to that of DNT (90%), although the latter provides about 20 times higher vapor concentration. The relatively strong quenching thus observed for TNT is likely due to its stronger oxidative power and larger driving force for the photoinduced electron transfer (FIG. 10). The former enhances electron donor-acceptor interaction between ACTC and TNT, while the latter facilitates the fluorescence quenching kinetics. The quenching response observed for the ACTC film is generally faster than that previously observed for other organic materials, consistent with the fibril porous structure of the film, which facilitates both gaseous adsorption and exciton migration across the film. The quenching efficiency obtained for ACTC films is higher than those previously reported for other explosive sensing materials at the same thickness.

Figure 20:
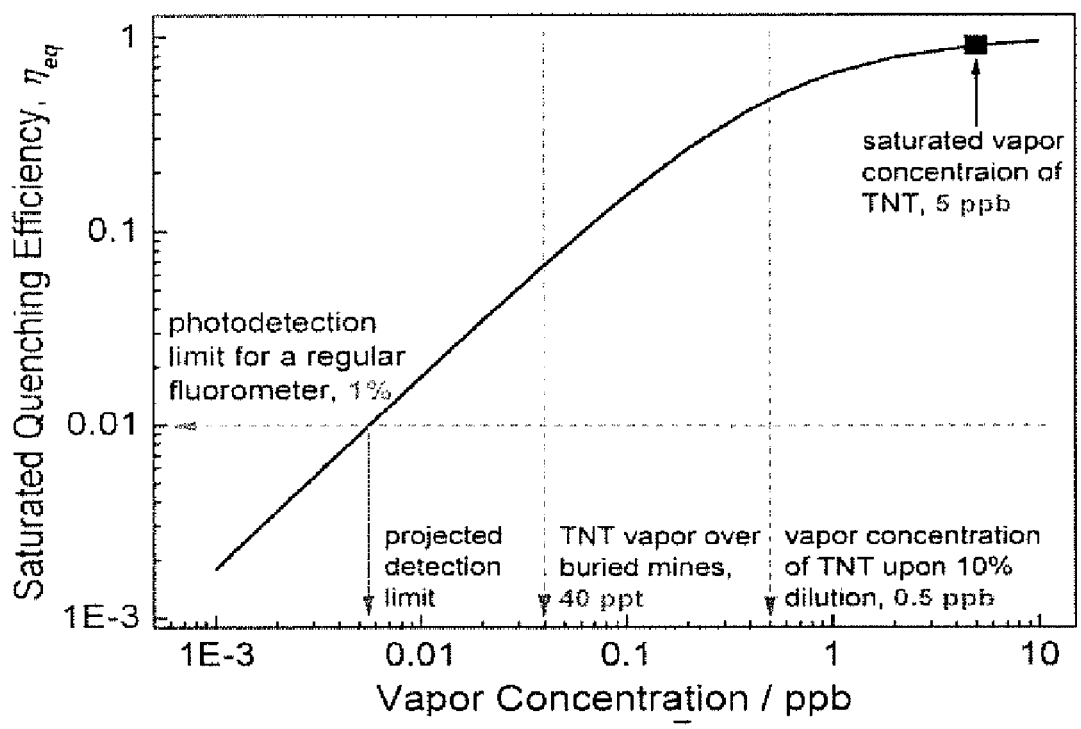
FIG. 20 shows Estimation of the detection limit for TNT of the ACTC nanofibril film.

The detection limit for TNT can be estimated with an assumption that the adsorption of TNT vapor follows the Langmuir equation (FIG. 20). Using the two data points measured in air (0 ppb of TNT) and saturated vapor pressure of TNT (5 ppb), a detection limit below 0.01 ppb can be deduced based on the measurement sensitivity of a regular fluorometer, one to a few percent change in intensity with a PMT detector. Such a projected detection limit is much lower than most (if not all) of the values previously reported for other organic sensory materials. This level of sensitivity is needed for detecting the trace vapor of explosives at a safe distance from the explosive device.

Example 7

Time Course of TNT Quenching Vs. Thickness of Films

Figure 21:
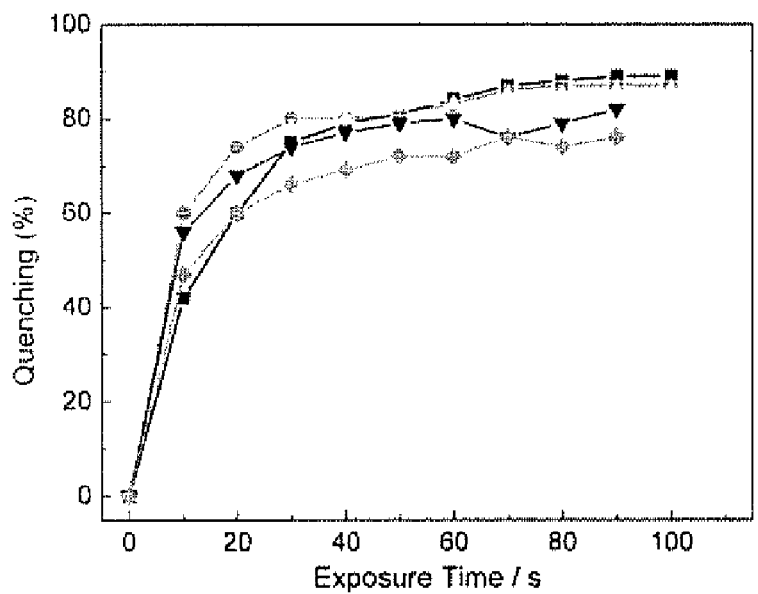
FIG. 21 shows Fluorescence quenching (%) of the ACTC film as a function of exposure time to TNT vapor. Five different thicknesses of films were employed: 90 nm (■), 72 nm (●), 54 nm (▲), 36 nm (▼), 18 nm (□)

FIG. 21 shows the full time-course of TNT quenching for 5 ACTC films with different thicknesses. Within the experimental error, no thickness-dependence was found for the whole time range of exposure. The response rate is approximately the same for all the five films studied. The slightly lower quenching found for the thinnest film was probably due to the evaporation of quencher molecules from the film during the course of transferring the sample from the explosives jar to the fluorometer. In general, a thin film (in porous structure) cannot hold the gaseous adsorbates as effectively as the thick films. We assume that with an in situ fluorescence monitoring the quenching efficiency of the thin film should be in the same range as the thick films.

Figure 22:
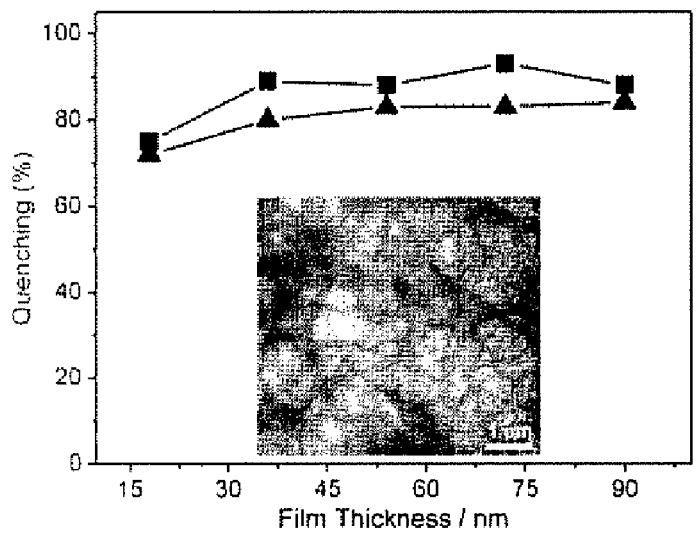
FIG. 22 shows Thickness dependence of fluorescence quenching efficiency of ACTC films. The quenching was tested upon exposing the film to saturated vapor of TNT (▲) and DNT (■) for 60 s. Inset: TEM image of a thin film of ACTC cast on silicon oxide from 2 mM THF solution.

The porous film morphology (inset of FIG. 22) and the extended one-dimensional pi-pi stacking enhance the access of quencher molecules to the excited states, thereby resulting in effective fluorescence quenching, which should be little dependent on the film thickness as is indeed evidenced by the observations shown in FIGS. 21 and 22. This behavior is in contrast to what was usually observed for other organic film sensors, for which the emission quenching efficiency was inversely proportional to the film thickness due to the diffusion limit of the exciton and the gaseous adsorbates. The thickness-independent film fabricated in this invention opens unprecedented opportunities for developing new types of sensors that can tolerate thick films. A thick film normally provides devices with improved reproducibility and sustainability.

Example 8

Recovery of Film Fluorescence by Exposure to Hydrazine

Figure 23:
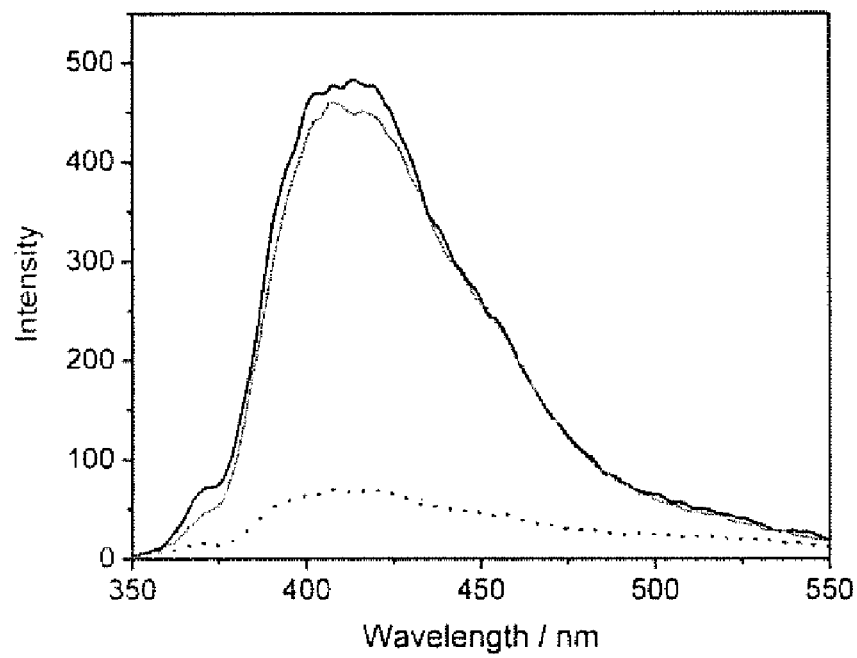
FIG. 23 shows Fluorescence spectra of a 90 nm ACTC film: pristine film (black-solid), after exposure to DNT vapor (5 ppb) for 60 s (black-dotted), after recovery in a hydrazine vapor (140 ppm) for 1 h (red-solid), and after second time exposure to the DNT vapor (red-dotted)

The fluorescence of ACTC film after exposure to explosives can be recovered simply by exposing the film to ambient air under dark. However such a recovery takes long time, usually a few days, to reach the fluorescence intensity of the pristine film. In this invention we found an effective way to speed up the recovery process by immersing the used film in a saturated vapor of hydrazine (ca. 140 ppm). As shown in FIG. 23, within only one hour the fluorescence was recovered about 90%. Upon immersing for longer time, 100% recovery could be obtained. Such a speedy recovery is favorable for developing the sensing materials in practical applications.

Figure 24:
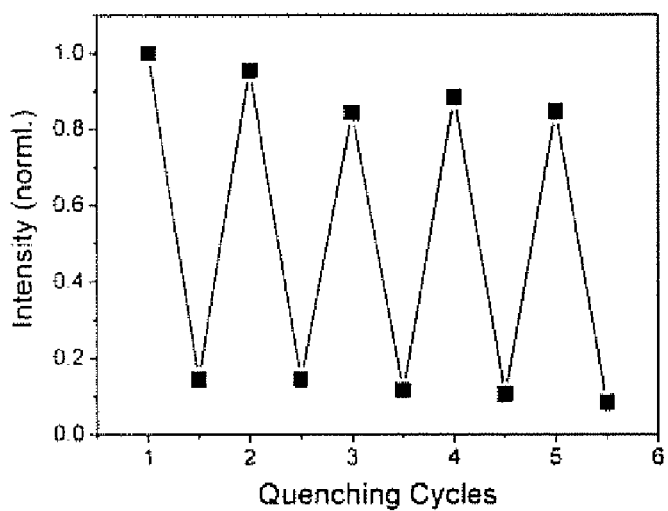
FIG. 24 shows Five continuous cycles of quenching-recovery test of a 90 nm ACTC film. The quenching was performed by exposing the film to a saturated vapor of DNT for 30 s. After each cycle of quenching, the fluorescence of the film was recovered by immersing it in a saturated vapor of hydrazine (ca. 140 ppm). All emission intensities are normalized to the intensity of the pristine film before exposure to DNT.

FIG. 24 shows five continuous cycles of fluorescence quenching-recovery tested with DNT. Efficient quenching was obtained for the film over repeated use, implying high stability of the film against photobleaching, a problem that is detrimental to organic sensors for their practical application.

Example 8

Quenching of Fluorescence of ACTC Film Upon Exposure to the Vapor of DMNB

Figure 25:
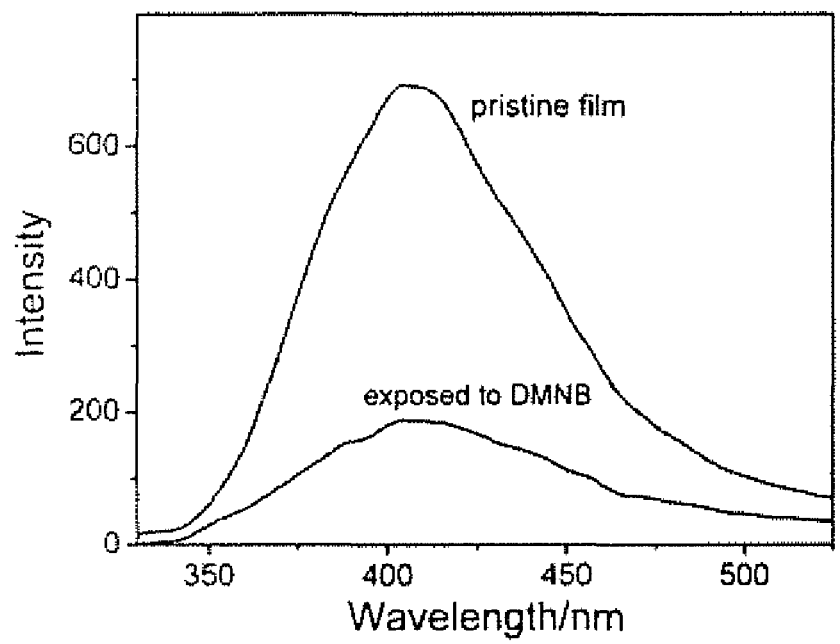
FIG. 25 shows fluorescence spectra of a 90 nm thick ACTC nanofibril film before and after exposure to the DMNB vapor (2.7 ppm) for 2 min.
Figure 27:
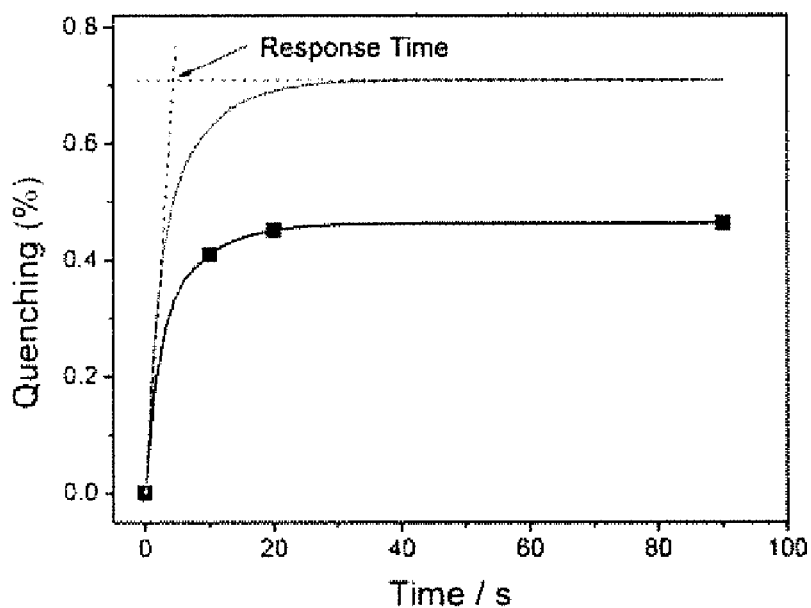
FIG. 27 shows Fluorescence quenching (%) of a 90 nm thick ACTC nanofibril film as a function of the time of exposure to DMNB vapor (2.7 ppm): black points and line represent the experimental data and the exponential fitting, respectively; red line represents the corrected time-course with consideration of the evaporation of DMNB during the transfer of the film from the DMNB jar to the fluorometer, for which the saturated quenching (%) at the adsorption equilibrium was set as 73%, the value obtained from the static quenching performed in the sealed cuvette as shown in FIG. 25.

The fluorescence spectra were measured on a LS 55 fluorometer (Perkin-Elmer) using either a cuvette holder or film sample holder. The saturated fluorescence quenching by DMNB was monitored by measuring the fluorescence spectra of the nanofibril film of ACTC before and after exposure to the saturated vapor of DMNB in a sealed cuvette, where the vapor pressure of DMNB remains constant, at 2.7 ppm. In case of measuring the time course of fluorescence quenching (as shown in FIG. 27), the measurement was performed as follows: Briefly, the fluorescence spectrum of the nanofibril film was measured immediately after immersing the film for certain amount of time inside a sealed-jar (50 mL) containing small amount of the DMNB powder. The longer the film was kept in the jar, the more fluorescence was quenched. By measuring the fluorescence of the film after different amounts of time of exposure to the DMNB vapor, a time-course of the fluorescence quenching was obtained. Typically, after about 10 seconds of exposure the surface adsorption of DMNB reached the equilibrium, leading to a saturation of the fluorescence quenching as shown in FIG. 27, where the quenching efficiency (%) is plotted as a function of the total amount of time of exposure to DMNB vapor. From such a plot, the time response of fluorescence quenching can be estimated for the ACTC nanofibril film. It should be noted that due to the high volatility of DMNB, the adsorbed DMNB molecules evaporated from the film during the course of transferring the sample from the DMNB jar to the fluorometer, thus resulting in lower quenching efficiency compared to that obtained in a sealed cuvette, as depicted in FIG. 25. To prevent direct contact of the film with the explosives analytes, some cotton was used to cover the explosives powder deposited at the bottom of the jar. Before use the jar was sealed for overnight to achieve constant, saturated vapor pressure inside. The presence of cotton also helps maintain a constant vapor pressure.

FIG. 25 shows the fluorescence spectrum of a 90 nm thick nanofibril film spin-cast from a THF solution of ACTC. Upon exposure to the saturated vapor (2.7 ppm) of DMNB, the fluorescence was quenched about 73%, nearly 4 times higher than that obtained for the conjugate polymer films. The higher quenching efficiency is likely due to the stronger reducing power of ACTC, in conjunction with the organized cofacial molecular stacking, which expedites the exciton migration along the nanofibers. The nanofibril film fabricated from ACTC possesses highly porous structure formed by the entangled piling of large number of nanofibers. The interconnected interstices thus formed provide continuous channels for expedient adsorption and diffusion of quencher molecules, which usually further facilitate the fluorescence quenching. Moreover, the free diffusion of quencher molecules across the film enables film-thickness independence for the fluorescence quenching as indeed observed for the quenching by TNT. This behavior is in contrast to what was usually observed for other organic film sensors, for which the emission quenching efficiency was inversely proportional to the film thickness due to the diffusion limit of the exciton and the gaseous adsorbates. For a film with sufficient thickness (e.g., 100 nm) to provide desirable sustainability and reproducibility for practical application in sensing, the nanofibril film fabricated in this study should provide a quenching efficiency at least one order of magnitude higher than the conjugate polymer films fabricated at the same thickness.

Figure 26:
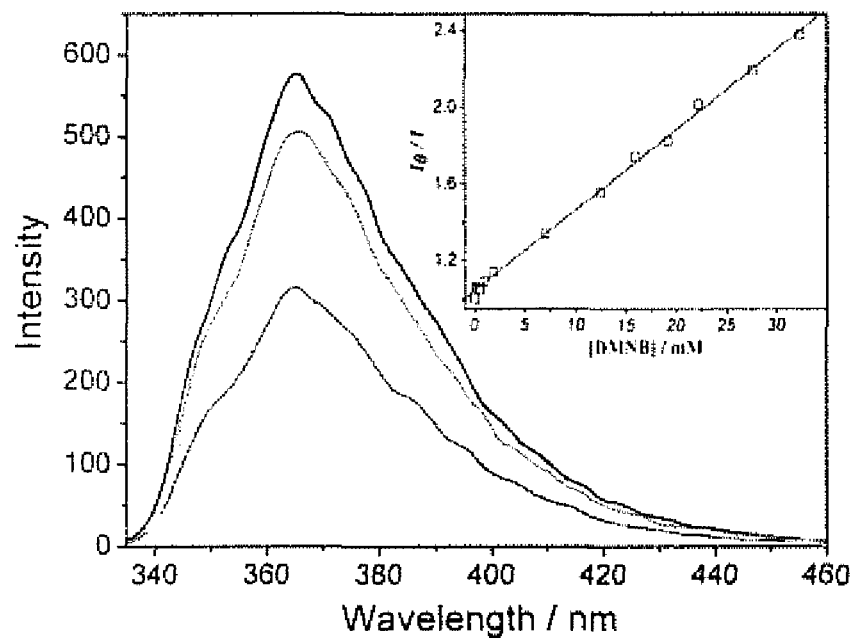
FIG. 26 shows Fluorescence spectra of a 20 micro-M ACTC solution in THF in the presence of different concentrations of DMNB: 0.0, 1.9, 7.0, 19.0 and 28.0 mM. Inset: Stern-Volmer plot of the fluorescence quenching.

The efficient fluorescence quenching was also observed for ACTC in solutions as shown FIG. 26, where the fluorescence spectra of an ACTC solution (20 micro-M in THF) were measured in the presence of different concentrations of DMNB. Upon addition of about 25 mM DMNB, the fluorescence of ACTC was quenched more than 50%. The Stern-Volmer plot (Inset of FIG. 26) of the quenching demonstrates linear dependence on the concentration of DMNB, implying a single mechanism (static or dynamic) for the fluorescence quenching. Considering the strong electron-donor-acceptor interaction between ACTC and DMNB, a static quenching mechanism is assumed for the observation shown in FIG. 26. A binding constant of $41\pm0.6$ M-1 is deduced form the slope of the Stem-Volmer plot. It is reasonable to assume that in the case of ACTC nanofibrils the surface binding (adsorption) with DMNB would be much stronger, mainly due to the higher density of ACTC molecules. The increased surface binding, in conjunction with the effective exciton migration along the nanofiber, enables amplified fluorescence quenching for the nanofibril films as evidenced in FIG. 25.

The highly porous structure of the nanofibril film also produces a fast response to quencher molecules, mainly due to the expedient diffusion within the nanofibril interstices. Indeed, within only about 10 seconds of exposure to DMNB vapor, the fluorescence quenching became saturated, reaching the adsorption equilibrium (FIG. 27). Fast quenching response is conducive for expedient onsite explosives detection. Compared to the quenching performed in a sealed cuvette as shown in FIG. 25, the saturated quenching efficiency obtained in FIG. 27 decreased by 30%, which is likely due to the evaporation of pre-adsorbed DMNB molecules from the film during the course of transferring the sample from the DMNB jar to the fluorometer. If the time-dependent quenching could be performed in situ in a sealed system (where the DMNB vapor remains constant), the time-course curve shown in FIG. 27 would have shifted up by 30% (as depicted by the red line shown in FIG. 27) to reach a saturated quenching efficiency of 73%, the value obtained from the static quenching in a sealed cuvette as shown in FIG. 25.

Figure 28:
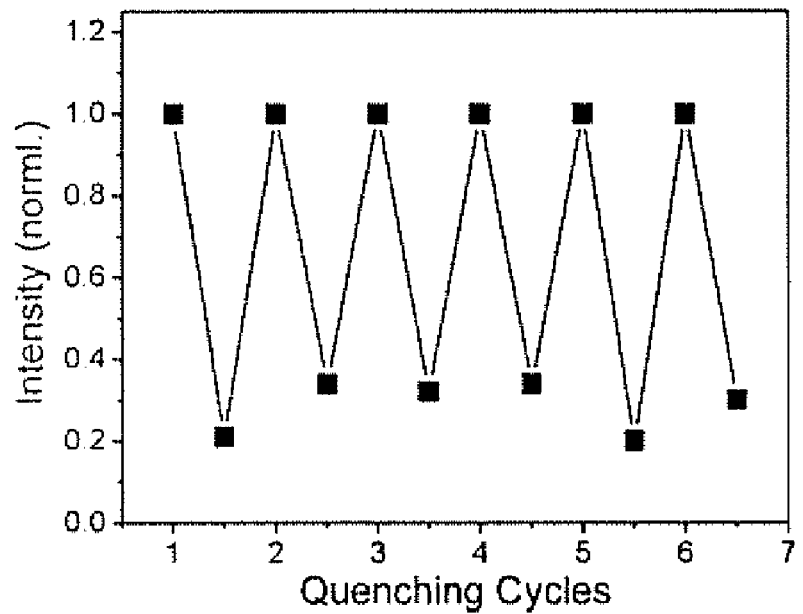
FIG. 28 shows Six continuous cycles of quenching-recovery test of a drop-cast ACTC film. The quenching was measured after exposing the film to the saturated vapor of DMNB for 5 min in a sealed cuvette. After each cycle of quenching, the fluorescence of the film was recovered by immersing it in the saturated vapor of hydrazine (ca. 140 ppm) for 1 h.

The effective fluorescence quenching observed above is solely due to the electron transfer from the excited sate of ACTC to DMNB. There is no possibility for excited state energy transfer, since the emission wavelength of ACTC is far above the absorption edge of DMNB. The photooxidized ACTC (still embedded in the nanofiber matrix) can be neutralized by strong reducing reagent like hydrazine, leading to recovery of the fluorescence. Indeed, the fluorescence of the nanofibril film after quenched by DMNB was recovered close to 100% after immersing the film in the saturated vapor of hydrazine (ca. 140 ppm) for 1 h. The recovered film demonstrated similar quenching efficiency when re-exposed to the DMNB vapor. FIG. 28 shows six continuous cycles of fluorescence quenching-recovery tested with saturated vapor of DMNB. Efficient quenching was obtained for the film over repeated use, implying high stability and sustainability of the film against permanent photobleaching, a problem that is usually detrimental to organic sensors for their practical application.

Figure 29:
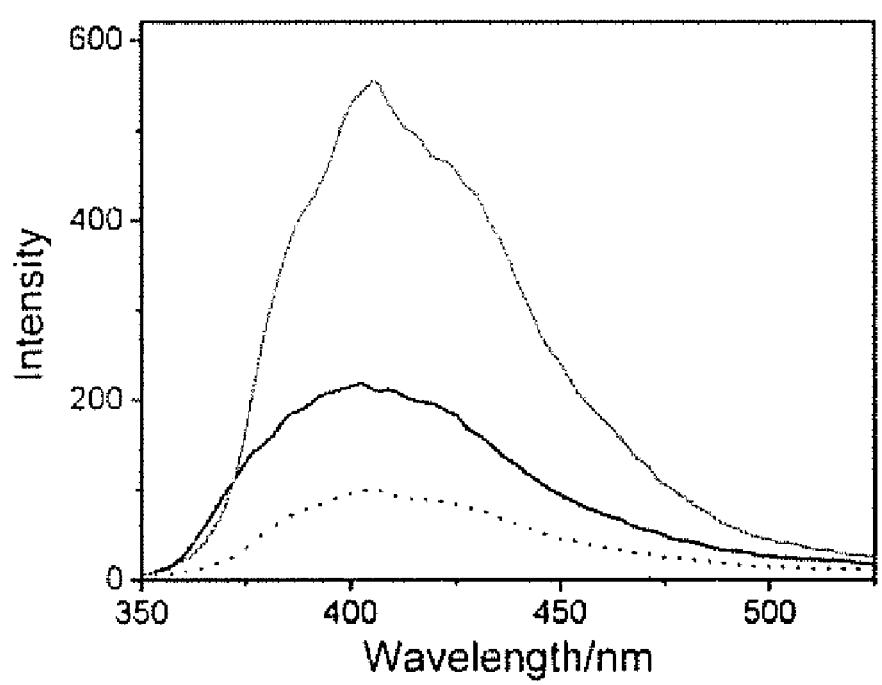
FIG. 29 shows Fluorescence spectra of a drop-cast ACTC film before (black-solid) and after immersing in a hydrazine vapor (140 ppm) for 2 h (red-solid). The spectrum of the hydrazine-fixed film after exposing to the DMNB vapor (2.7 ppm) for 5 min is also shown (black-dotted)

In this invention, even for the pristine nanofibril film, which is intrinsically intercalated with small number of oxygen molecules or the analogous oxidized trap sites, the fluorescence of the film was dramatically enhanced upon immersing it in a hydrazine vapor for extended time. FIG. 29 shows the fluorescence spectra of an ACTC film drop-cast from a 1 mM THF solution before and after immersed in 140 ppm hydrazine vapor for 2 hour (followed by blowing of nitrogen to remove the hydrazine condensation). About two times increase in fluorescence intensity was obtained after 'healing' the film with hydrazine. Exposing the film to hydrazine for longer time (up to 6 h) did not resulted in further enhancement in fluorescence, implying an expedient fixation of the oxidized defects by hydrazine. Compared to the fluorescence spectrum of the pristine film, the spectrum obtained after exposure to hydrazine became narrower and shifted to longer wavelength, characteristic of enhanced, more organized molecular stacking as observed for other planar aromatic molecules. The enhanced molecular stacking thus observed might be due to the removal of the intercalated oxygen or the oxidized defects. The fluorescence quenching efficiency is primarily determined by the exciton migration along the nanofibers, which in turn is dependent on the extent of molecular stacking and organization. The enhanced molecular stacking obtained for the hydrazine-healed film should demonstrate increased fluorescence quenching by DMNB. Indeed, upon exposing the 'healed' film to DMNB vapor (2.7 ppm), the fluorescence was quenched by 83%, significantly more effective than that observed for the pristine film as shown in FIG. 25 (where 73% quenching was observed). The degree of quenching (if defined as I0/I, as usually used in Stern-Volmer equation) of the former, 5.9, is about 60% higher than that obtained for the latter, 3.7.

Example 9

Fabrication and Microscopy Characterization of ACTC Nanofibers

Method 1. Gelation: Ultrafine nanofibrils of ACTC were fabricated through a gelation process in cyclohexane. Briefly, a certain amount of ACTC (1 mg/mL) was added to cyclohexane, followed by sonication for 5 min. A milk-like suspension was thus obtained. Upon heating in an oil bath at 100° C., the suspension became totally dissolved in a few min, producing a transparent solution. With cooling in air (room temperature), the solution turned to be little turbid within a few min as the molecular aggregation started. After about 5 min, the gelation started as revealed by the phase immobilization. Leaving the sample open in a hood led to the formation of an aged gel within about one hour.

The gel thus made is very tender, and can be transferred simply by pipetting. The sample for AFM measurement was prepared by spin-casting one drop (of disposal glass pipette) of the gel onto a cleaned glass cover slip at 2500 rpm. For TEM measurement (which demands minimal deposition of sample to afford sufficient electron transmission), the gel had to be diluted with a proper solvent (e.g., cyclohexane) before being deposited onto the copper grids.

Method 2. Phase Transfer: Uniform nanofibers of ACTC were also fabricated through a so-called 'phase transfer' method, which has been developed in our lab for assembling large, planar aromatic molecules into one-dimensional nanostructures (e.g., nanowires). Briefly, the molecular assembly was processed through slow crystallization at the interface between a 'good' and a 'poor' solvent, where the slow 'phase transfer' between the two solvents decreases the solubility at the interface. The poor solvent (e.g., methanol) is normally quite different (e.g., in term of polarity) from the good solvent (e.g., chloroform), thus providing the possibility to keep the two solvents in separate phases for an extended period. Typically, a larger amount (>10:1 vol) of 'poor' solvent was transferred atop a concentrated chloroform solution of the molecule (1 mM) in a test tube. Within minutes, crystallization (precipitation) occurred at the interface, followed by slow diffusion into the upper phase of the 'poor' solvent. The crystals thus formed can be transferred and cast onto glass surface by pipetting. In this study, the 'good' solvent used was chloroform, and methanol was used as the 'poor' solvent.

Method 3. Rapid Dispersion: Nanofibril self-assembly of ACTC was also performed through fast precipitation by rapidly dispersing the molecules from a 'good' solvent (such as chloroform) into a 'poor' solvent (such as methanol), where the molecule has limited solubility and thus self-assembly of molecules is expected to occur instantaneously. Briefly, a minimum volume of concentrated chloroform solution (1 mM) of ACTC was injected rapidly into a larger volume (1:20 vol) of methanol, followed by immediate mixing with pipette. Such a self-assembly approach takes the advantage of the strong intermolecular pi-pi interaction, which is enhanced in a poor solvent due to the solvophobic interaction. Uniform nanofibers were obtained for ACTC via such rapid dispersion method, as evidenced by the TEM images shown in FIG. 32. However, the same method produced only ill-defined aggregates for TDTC, largely due to its saddle-like molecular geometry.

Figure 30:
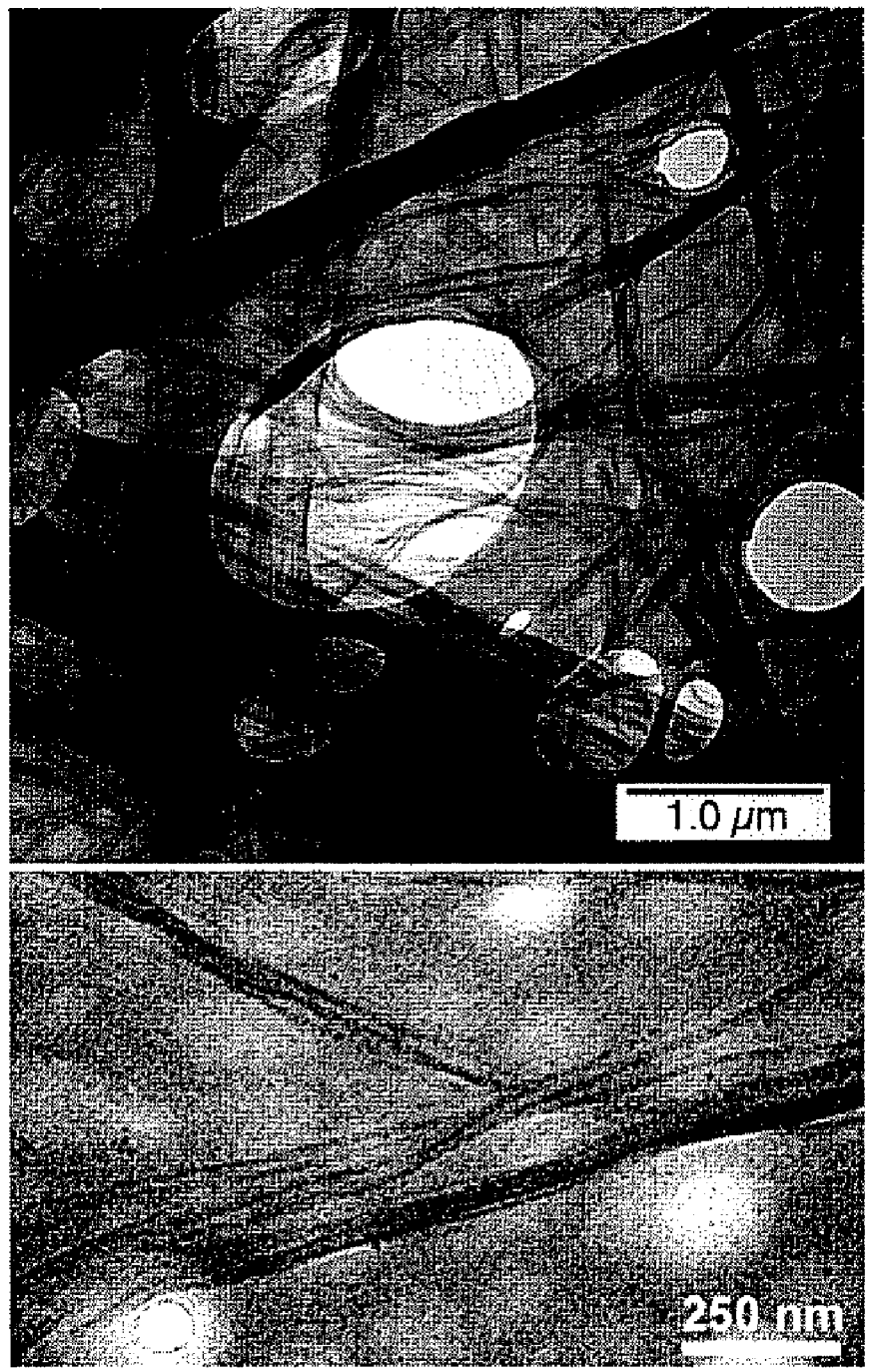
FIG. 30 shows TEM images of ACTC gel deposited on holey carbon films. The zoomed-in image (low panel) shows single nanofibers separated from bundles by dilution into cyclohexane (~5% vol dilution)

Gelation of the molecules is typically processed by cooling a hot, homogeneous solution from an elevated temperature to room temperature. Such a gelation process decreases gradually the molecular mobility (dynamics), and thus minimizes the lateral growth of molecular assembly due to side-chain association. The coplanar geometry of ACTC provides the molecule with stronger pi-pi interaction, and thus more organized molecular stacking. Indeed, uniform nanofibers were successfully obtained for ACTC at concentration of 1 mg/mL. FIG. 30 shows the TEM images of the nanofibers thus formed deposited on holey carbon film, where long fibers with large aspect ratio are clearly seen all over the substrate, implying a morphological signature of that the gelation of ACTC is primarily due to the columnar stacking of the macrocycles. Due to the strong hydrophobic association between the alkyl side chains, most of nanofibers are parallel stuck together as bundles or entangled as fibril piles.

High magnification imaging shows separate nanofibers as depicted in the low panel of FIG. 30. Average diameter of the nanofiber is ca. 10 nm, which corresponds to a cross-section size of nine (3×3) ACTC molecules laterally associated with full interdigitation of side-chains. The nanofibers thus fabricated are far smaller than most of the nanofibers fabricated from polymers, oligomers or other planar aromatic molecules, including those discotic molecules. A small cross-section is usually not thermodynamically favorable for organic nanofibrils with large aspect ratios. The success of fabricating uniform ultrafine nanofibers from ACTC is mainly due to the strong multiple side-chain interdigitation between the molecules, which is facilitated by the coplanar geometry of the molecules. The lateral supra-molecular assembly formed by multiple side-chain interdigitation has recently been observed for other AEMs on surfaces by STM. The ultrafine nanofibers thus fabricated provide increased surface area, which will potentially enhance the surface adsorption, and thus sensing efficiency when used as sensor materials for VOCs. Moreover, a film consisting of large number of these ultrafine nanofibers piled together will produce largely porous structure to facilitate the diffusion of gaseous molecules across the film, potentially leading to a sensor material with sensing efficiency that is independent on the film-thickness.

Figure 31:
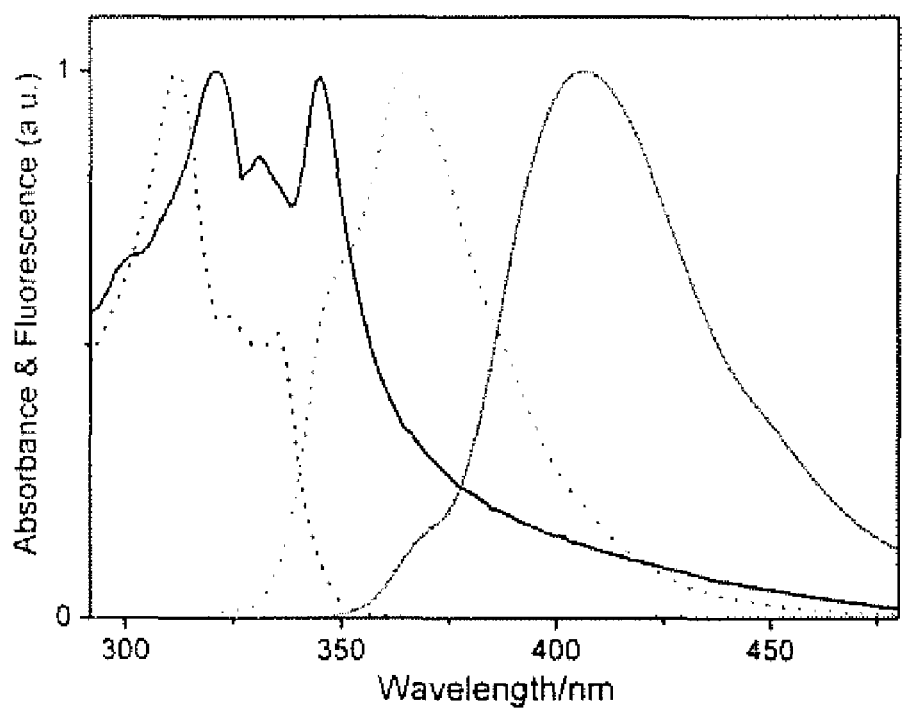
FIG. 31 shows Absorption (black) and fluorescence (red) spectra of molecularly dissolved solution (dotted) and cast-film (solid) of ACTC. The solution used for spectral measurement was 1 micro-M in THF. The film was cast from an ACTC gel (3 times diluted in cyclohexane). All spectra normalized to the maxima.

Consistent with the strong pi-pi stacking as implicated by the preferred one-dimensional self-assembly, the electronic property of the ACTC molecule, which is principally determined by the conjugate structure of the core scaffold, is significantly altered when assembled into the fiber (FIG. 31). Compared to the absorption spectra of molecules dissolved in solutions, the absorption spectrum of the nanofibers deposited on glass is red-shifted by 10 nm, and the absorption transition at the lower energy is relatively enhanced. Upon assembly, the fluorescence of individual molecules (centered at 365 nm) is quenched due to the strong pi-pi interaction, and instead a new fluorescence band emerges at longer wavelength, around 405 nm. These spectral changes are characteristic of pi-pi stacked molecular aggregate, for which the collective electronic features are significantly different from the individual component molecules.

In addition to the sol-gel processing, a phase transfer method (based on slow crystallization at the interface between a good and a poor solvent), was also exploited for the self-assembly of ACTC. The coplanar configuration of ACTC is expected to facilitate the cofacial molecular stacking, and thus the one-dimensional growth of the molecular assembly. Indeed, uniform nanofibers were obtained by phase transfer between a concentrated chloroform solution and an excess of methanol solvent. FIGS. 32A and B show the TEM images of the nanofibers deposited on silicon oxide substrates. The average size of the nanofibers is ca. 40 nm, about 4 times larger than those prepared from the sol-gel processing, likely due to the faster precipitation (crystalline growth) of molecules in methanol compared to the slow crystallization in gradually cooled cyclohexane.

Figure 32:
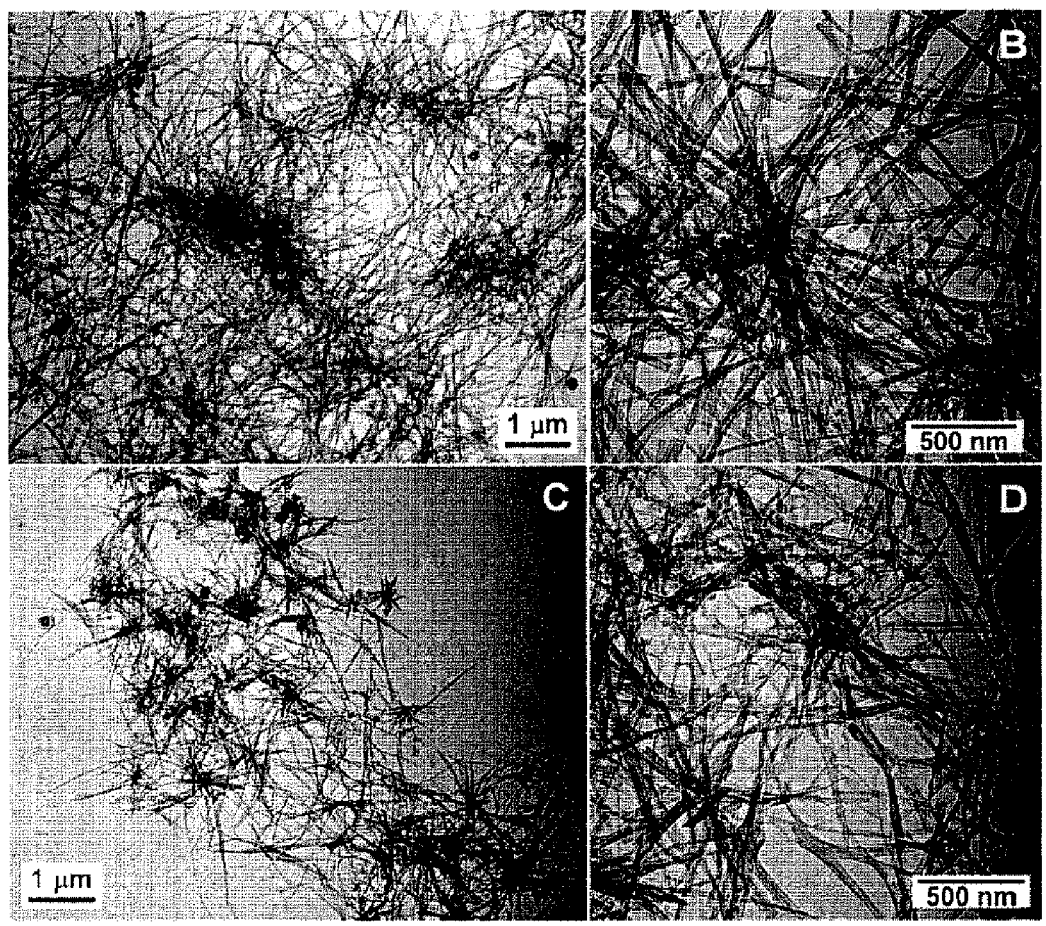
FIG. 32 shows (A, B) Large-area and zoomed-in TEM image of ACTC nanofibers fabricated by the phase-transfer crystallization between excessive methanol and a concentrated chloroform solution (1.0 mM). (C, D) Large-area and zoomed-in TEM image of ACTC nanofibers fabricated by rapid dispersion of a concentrated chloroform solution (1.0 mM) into a large volume of methanol (1:20 vol). All the TEM samples were prepared by depositing the nanofibers on silicon oxide grids.

Interestingly, as shown FIG. 32, the nanofibers are likely formed through a seeded self-assembly processing, for which the initially formed nanocrystals act as the one-dimensional crystalline growing seeds. Similar self-assemblies were previously observed for other organic molecules. Such seeded one-dimensional self-assembly is consistent with the initial fast mixing of the two solvents within the thin layer of interface, where the rapid decrease of solubility leads to production of large number of small nanocrystals, followed by slow diffusion of more molecules from the chloroform phase into the interface to initiate the one-dimensional growth of nanofibers from the core-seeds. The seeding-induced nanofiber growth can be seen more clearly in the fabrication by rapid dispersion (FIGS. 32C and D), where the fast injection of large amount of methanol into a small volume of chloroform solution (1:20) created larger number of nanocrystals. The more seeds created, the more competitive it is for the free molecules for the later stage of fibril growth. Indeed, under the same starting concentration of ACTC, the nanofibers fabricated via the fast dispersion were shorter than those fabricated from the phase transfer.

Example 10

Figure 33:
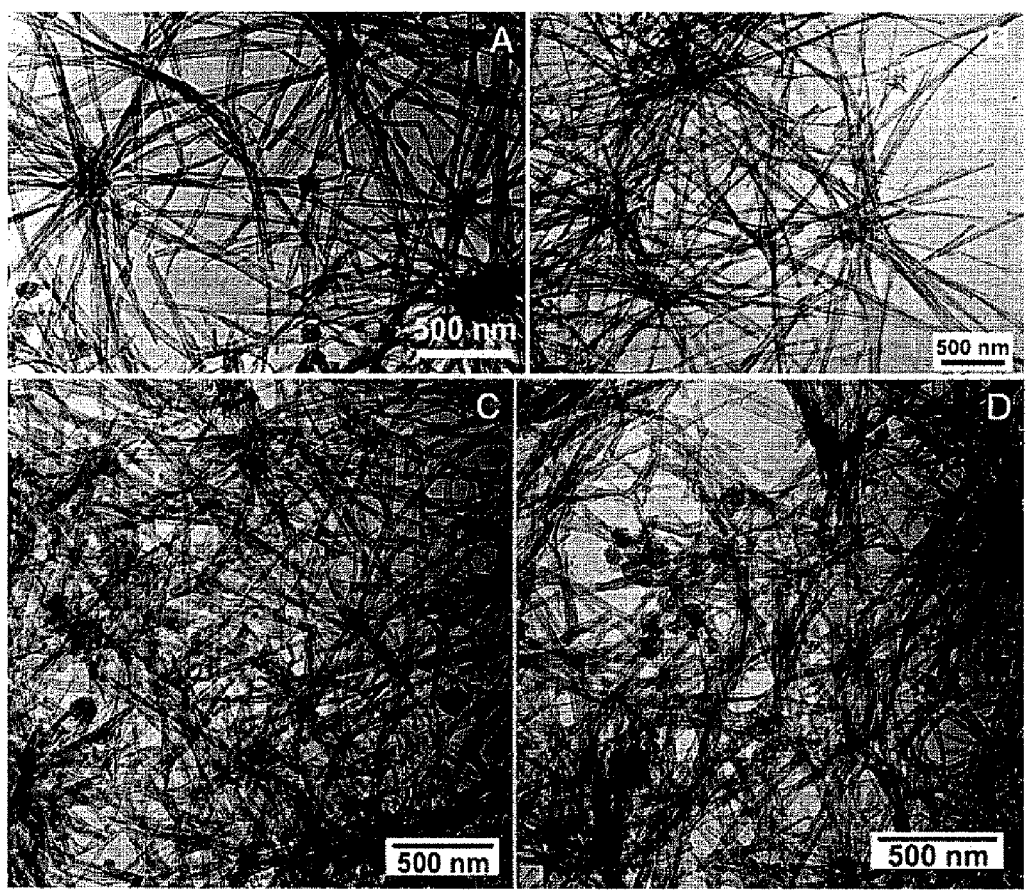
FIG. 33 shows (A, B) TEM images of ACTC nanofibers prepared by the phase-transfer crystallization between excessive methanol and a concentrated chloroform solution (1.0 mM): A) as prepared nanofibers, deposited on holey carbon grids; B) 5 weeks after stored in the solution, deposited on silicon oxide grids. (C, D) TEM images of ACTC nanofibers prepared by rapid dispersion of a concentrated chloroform solution (1.0 mM) into a large volume of methanol (1:20 vol): C) as prepared, deposited on holey carbon grids; D) 5 weeks after stored in the solution, deposited on silicon oxide grids. Note: the images C and D were taken intendedly from the thick area to reveal the fibril porous morphology that is conducive to gaseous sensing as discussed in the context.

Stability and Sustainability of ACTC Nanofibers for Storage and Substrate transfer The strong pi-pi stacking between planar ACTC molecules provides the nanofibril structure with sufficient mechanical integrity to be transferred onto different substrates. Compared to the polar substrate of silicon oxide as used in FIG. 32, a non-polar substrate, holey carbon film, was also employed for TEM imaging of the nanofibers (FIG. 33). Same morphology and fiber distribution were found for the nanofibers deposited on carbon films. This robust, durable character of the nanofibers, which allows for expedient handling and deposition onto various substrates, is critical for approaching practical applications of the nano-assembly. More interestingly, the nanofibers assembled in solutions demonstrated strong stability (against Ostwald ripening) as evidenced in FIG. 33, where the nanofibers stored (aged) in the assembling solution for more than one month were deposited onto both silicon oxide and carbon films, and showed the same size and morphology as those freshly fabricated.

The high stability of ACTC nanofibers against Ostwald ripening (i.e., formation of large agglomeration) was examined by TEM imaging of both the freshly prepared nanofibers and those stored in the methanol suspension for more than one month. As shown in FIG. 33, for both the nanofibers fabricated from phase-transfer and rapid-dispersion, no significant change in size, morphology or fibril distribution was found between the as-prepared nanofibers and those aged for 5 weeks. Moreover, by depositing the nanofibers on different kinds of grids (carbon vs. silicon oxide) the sustainability of the nanofiber for substrate transfer was also examined as shown in FIG. 33. For the two substrates under investigation, no significant surface effect was observed for the nanofibers fabricated from the two self-assembling methods. Such robust sustainability (against substrate influence) makes it feasible and convenient to deposit the nanofibers on various surfaces for future device fabrication. In contrast, many other organic nanofibers suffer from the structure or morphology damage when transferred to solid substrates.

Example 11

Uniaxial Optical Property of ACTC Nanofibril

Figure 34:
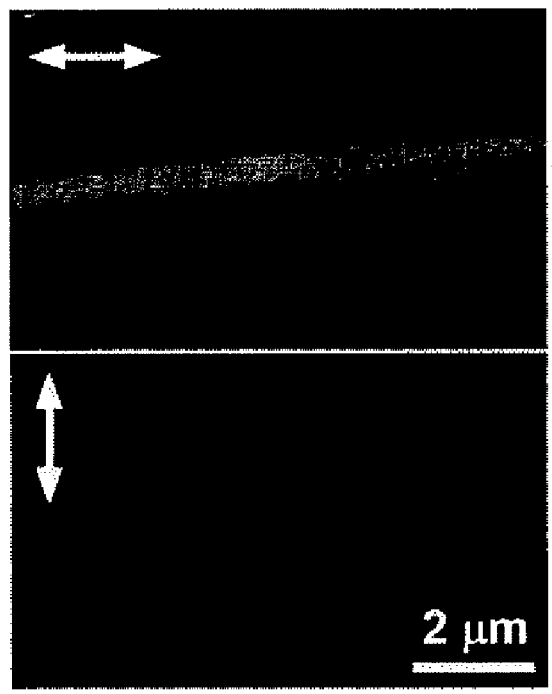
FIG. 34 shows Fluorescence microscopy image of a single ACTC nanofiber under linearly polarized excitation (340-380 nm). The direction of excitation polarization is marked as the arrow.

Considering the one-dimensional morphology of the nanofiber, which is primarily controlled by the pi-pi stacking, the nanofiber should demonstrate strong anisotropy in intermolecular electronic coupling, i.e., approximately uniaxial optical property along the long axis of the nanofiber. This is similar to the uniaxial columnar packing of other planar aromatic molecules and discotic liquid crystal molecules. FIG. 34 shows the fluorescence microscopy image of a single ACTC nanofiber under linearly polarized excitation (340-380 nm). Depending on the orientation of a nanofiber with respect to the excitation polarizer, the fluorescence intensity measured for the nanofiber changes from the minimum when the polarizer is perpendicular to the long axis of the nanofiber, to the maximum when the polarizer is oriented parallel to the nanofiber. Such linearly polarized emission is consistent with the one-dimensional pi-pi stacking, which often possesses a transition dipole parallel to the direction of p-p stacking (i.e., perpendicular to the molecular plane), as recently evidenced in cofacially stacked dimers of other planar aromatic molecules (e.g., phenalene).

Example 12

Fluorescence Quenching of ACTC Nanofibrils Upon Exposure to DNT Vapor

The one-dimensional molecular stacking between planar aromatic molecules is usually conducive to excited sate (exciton) migration via cofacial intermolecular electronic coupling. Thereby, extended exciton diffusion would be expected for the ACTC nanofiber along the long axis, enabling amplified fluorescence quenching by surface adsorbed quenchers. Deposition of large number of the nanofibers onto a glass substrate would form a highly porous film consisting of entangled piling of the nanofibers as depicted in the TEM images (FIGS. 32 and 33). Such a nanofibril film not only provides increased surface area to enhance the adsorption of gaseous molecules, but also enables expedient diffusion of quencher molecules across the film matrix. Combination of the porous characteristic with the extended exciton migration intrinsic to the individual nanofiber makes the nanofibril film a potentially effective sensing material for detecting oxidative VOCs, particularly the nitro aromatic explosives, which act as electron acceptors to quench the fluorescence of nanofibers.

Figure 35:
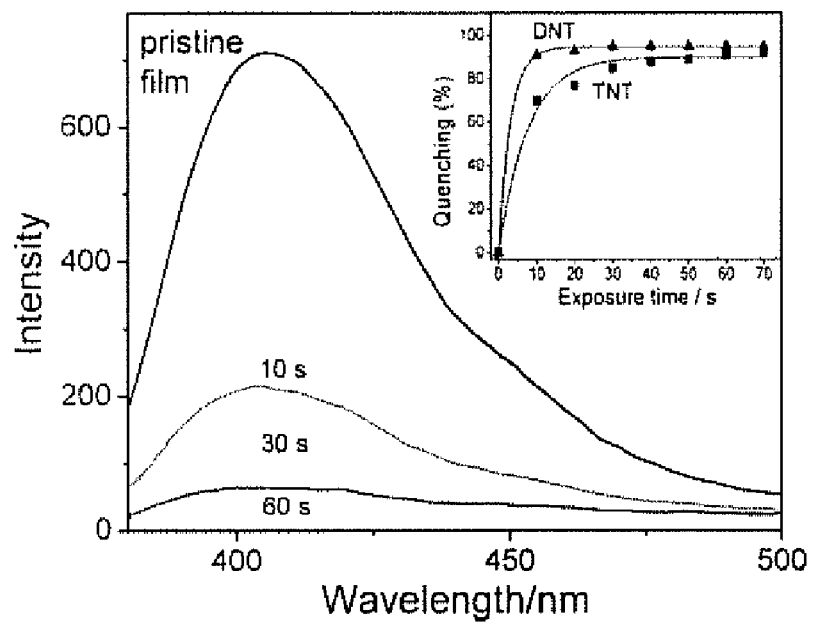
FIG. 35 shows Fluorescence spectra of a thin layer of ACTC nanofibers (deposited from the gel) upon exposure to saturated vapor of TNT (5 ppb) at different times. Inset: time-course of fluorescence quenching for TNT and DNT. Before use in the quenching, the deposited film was dried in a vacuum oven at 60° C. for 3 h. Average thickness of the film: 75 nm.

FIG. 35 shows the fluorescence quenching of an ACTC nanofibril film upon exposure to two explosives compounds, 2,4-dinitrotoluene (DNT) and 2,4,6-trinitrotoluene (TNT), which both exist in commercial explosive products and have been widely exploited for the purpose of evaluating explosive sensing devices. The nanofibril film was fabricated by casting the ACTC gel (2× diluted in cyclohexane) onto a glass substrate, followed by annealing in vacuum at 60° C. for 3 h to remove the encapsulated solvent. The film thus fabricated is about 75 nm in thickness, and is strongly fluorescent, with a quantum yield of 0.19. Upon exposure to saturated vapor of DNT (100 ppb) or TNT (5 ppb), the fluorescence of the film was dramatically quenched (FIG. 35). Since the fluorescence wavelength of ACTC is far above the absorption range of the two explosives, and thus there is no possibility for excited state energy transfer, the observed fluorescence quenching must explicitly be due to the photoinduced electron transfer from the excited ACTC to the quencher. Such a photoinduced electron transfer is highly favored by the large driving forces (2.4 eV and 1.9 eV for TNT and DNT, respectively).

As shown in the inset of FIG. 5, the quenching response, ca. 10 s, is much shorter those observed for other organic or polymer based sensory materials. For the conjugate polymer films developed by others, even at a thickness of only 2.5 nm, the quenching response (ca. 100 s) was still about one order of magnitude slower than that obtained for the nanofibril film. The faster response obtained for the nanofibril film is apparently due to the highly porous structure formed by the entangled piling of the nanofibrils, which facilitates the diffusion of gaseous molecules across the film. The slightly faster response obtained for DNT is likely due to the higher vapor pressure of DNT. Upon extended exposure to the explosives, the fluorescence quenching eventually becomes saturated when reaching the adsorption equilibrium. It is remarkable to note that at the adsorption equilibrium (after ca. 40 s of exposure) the quenching efficiency of TNT (90%) was comparable to that of DNT (95%), although the latter provides about 20 times higher vapor pressure. The relatively strong quenching thus observed for TNT is likely due to its stronger oxidative power and larger driving force for the photoinduced electron transfer. The former enhances electron donor-acceptor interaction between ACTC and TNT, while the later facilitates the fluorescence quenching kinetics. The quenching efficiency obtained for the nanofibril films is much higher than those previously reported for other explosive sensing materials fabricated at the same thickness.

Figure 36:
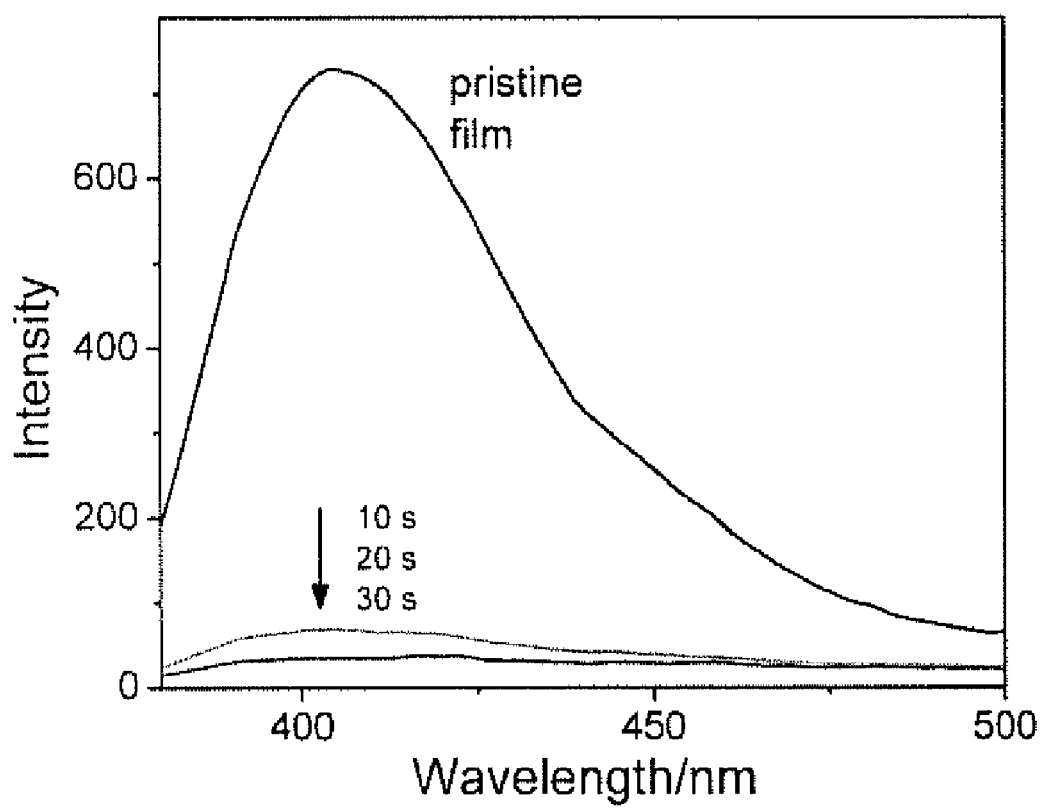
FIG. 36 shows Fluorescence spectra of a 75 nm thick nanofibril film upon exposure to saturated vapor of DNT (100 ppb) at different times.

As performed for TNT, the DNT quenching was also monitored by measuring the fluorescence spectra of the nanofibril film (75 nm thick) at different time intervals of exposure to the saturated vapor of DNT (FIG. 36). Within only 10 s after exposure, the fluorescence was quenched close to 95%. Further exposure did not increase the quenching significantly, implying a fast response to DNT vapor, with regard to reaching the adsorption equilibrium.

Example 13

Figure 37:
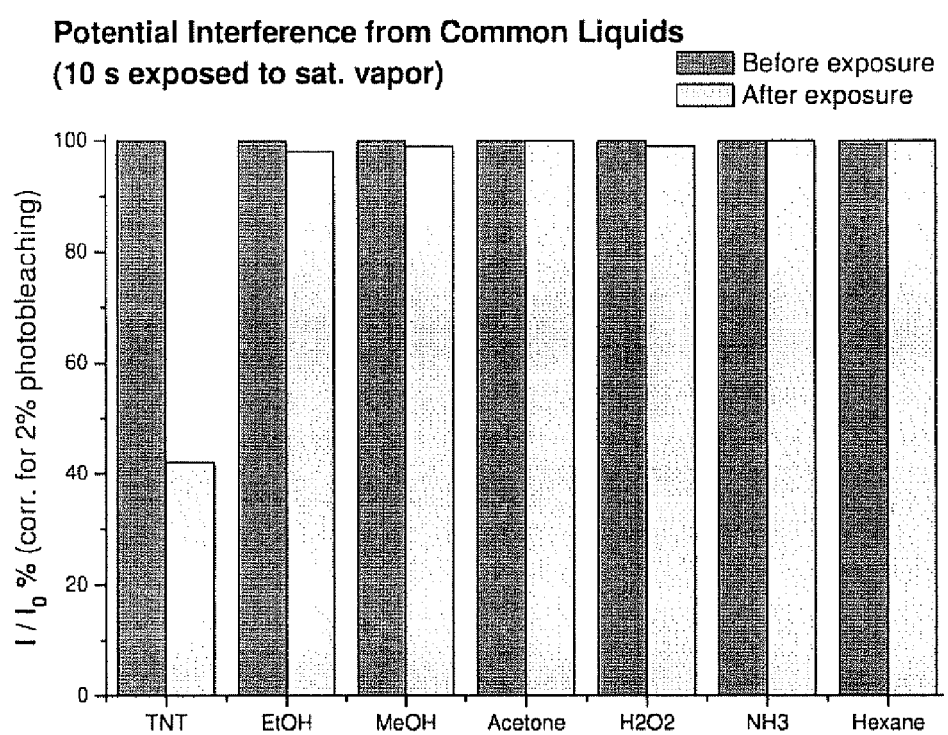
FIG. 37 shows the fluorescence quenching efficiency of an ACTC nanofibril film upon exposure to the saturated vapor of different liquids, in comparison to the exposure to the saturated vapor of TNT (5 ppb).
Figure 38:
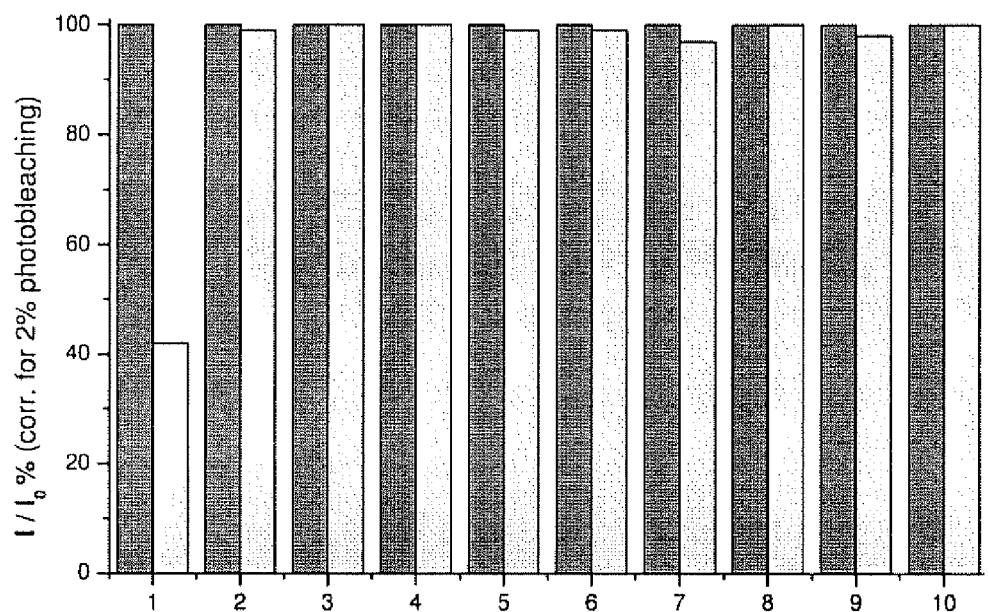
FIG. 38 shows the fluorescence quenching efficiency of an ACTC nanofibril film upon exposure to the saturated vapor of different cosmetic products, in comparison to the exposure to the saturated vapor of TNT (5 ppb).
Figure 39:
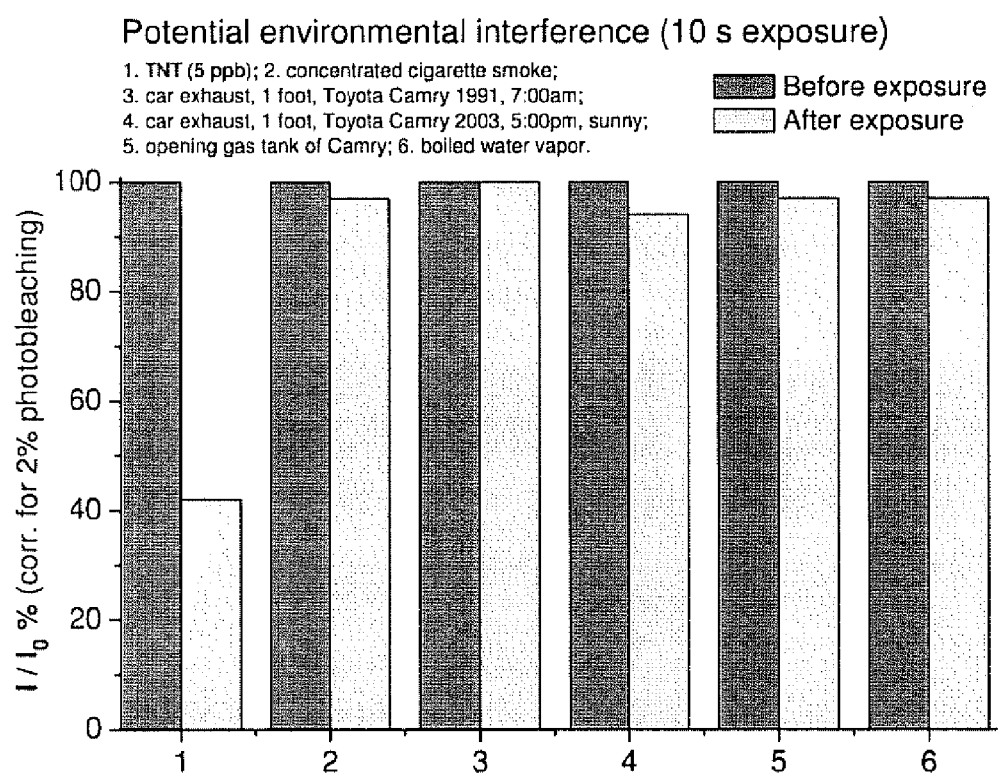
FIG. 39 shows the fluorescence quenching efficiency of an ACTC nanofibril film upon exposure to or being placed in different environmental situations, in comparison to the exposure to the saturated vapor of TNT (5 ppb).

Sensing Selectivity of ACTC Nanofibrils for TNT Against Various Environmental Interfaces The nanofibril sensors described above also demonstrates ideal persistence against the potential interference from the common environmental backgrounds, for which about 10 different liquids (e.g., water, alcohols, gasoline, acetone, etc.) and 10 various cosmetics (including perfumes, creams, shampoo, hair spray, etc.) were employed to provide the background vapor at the saturated pressure. The similar sensing persistence (selectivity) was also examined by testing the nanofibril sensor in some extreme cases, such as exposure closely to a car exhaust pipe and heavy personal smoking, to check the potential influence of $CO_2$ and the nitrogen oxide gases. In all these cases, no significant fluorescence quenching was observed, whereas for the same film about 60% quenching was obtained upon exposure to 5 ppb TNT. Some typical results showing the sensing selectivity are presented in FIGS. 37-39.

While the invention has been explained in relation to exemplary embodiments, it is to be understood that various modifications thereof will become apparent to those skilled in the art upon reading the description. Therefore, it is to be understood that the invention disclosed herein is intended to cover such modifications as fall within the scope of the following claims.

The invention claimed is:

1. A sensor comprising:
a film including an entangled piling comprising a plurality of organic nanofibrils, each of the plurality of organic nanofibrils consisting of one-dimensionally arranged arylene-ethynylene macrocycle molecules along a long axis of each of the plurality of organic nanofibrils in a cofacially stacked arrangement,
wherein the arylene-ethynylene macrocycle molecule comprises at least three arylene groups covalently bonded by triple carbon-carbon bonds in a rigid, planar, ring structure and wherein its backbone comprises a continuous pi-conjugate bond pathway, which provides strong adsorption of electromagnetic radiation, and wherein the film is capable of emitting strong fluorescence radiation with a quantum yield of ca. 20% or above, the emitted radiation of the film is decreased upon exposure to explosives vapor and other oxidative molecules.

2. The sensor as in claim 1, wherein the continuous pi-conjugate bond pathway is altered by the substitution of functional moieties at the backbones, thus leading to change in the wavelength and absorptivity of the absorption of the arylene-ethynylene macrocycle molecule, or leading to change in the wavelength and quantum yield of the emission of the arylene-ethynylene macrocycle molecule.

3. The sensor as in claim 1, wherein the backbone is in the shape selected from the group consisting of triangle, square, pentagon, hexagon, or combinations thereof.

4. The sensor as in claim 1, wherein the backbone is in different sizes, ranging from 0.5 nm to above 10 nm.

5. The sensor as in claim 1, wherein the backbone consists of different chemical groups at the corners or edges of the arylene-ethynylene macrocycle molecules, the chemical groups including different functional moieties, chromophores, and in different conjugate structure.

6. The sensor as in claim 1, wherein the backbone is modified by substitution with different chemical groups at the corners or edges of the arylene-ethynylene macrocycle molecules, the substitutions functioning as side chains, the side chains affecting the strength and conformation of the molecular arrangement of the of the arylene-ethynylene macrocycle molecules within the each of the plurality of organic nanofibrils.

7. The sensor as in claim 6, wherein the strength and conformation of the co-facial stacking of between the arylene-ethynylene macrocycle molecules affect the exciton, migration and charge transport along, and thus affect the sensing efficiency of each of the plurality of organic nanofibrils when used as fluorescent sensory materials.

8. The sensor as in claim 1, wherein the backbone can be modified by substitution with different chemical groups at the corners or edges of the arylene-ethynylene macrocycle molecules, and the substitutions can be connected to the backbone with different linkers.

9. The sensor as in claim 8, wherein the linkers may be in conjugation with the backbone, affecting the absorption and emission capability of the backbone.

10. The sensor as in claim 8, wherein the linkers affects the configuration between the side chains and the backbone, resulting in different conformations of the whole arylene-ethynylene macrocycle molecule, including both the central backbone and all the side chains, the conformation affecting the strength and conformation of the molecular arrangement of the arylene-ethynylene macrocycle molecules within each of the plurality of organic nanofibrils.

11. The sensor as in claim 1, wherein the arylene-ethynylene macrocycle molecules absorb and emit fluorescence ranging from ultraviolet to visible region.

12. The sensor as in claim 1, wherein the film is highly porous, providing
strong adsorption and efficient diffusion of explosives molecules across the film matrix.

13. The sensor as in claim 1, wherein the film is fabricated by casting a solution containing the arylene-ethynylene macrocycle molecule onto a substrate, followed by drying in air and then vacuum at elevated temperatures.

14. The sensor as in claim 13, wherein film thickness and the density of the plurality of organic nanofibrils thus packed in the film are defined by the concentration of the solution.

15. The sensor as in claim 13, wherein the substrate is a glass or any other flat substrate that provides strong affinity with the arylene-ethynylene macrocycle molecules and plurality of organic nanofibrils.

* * * * *